US009039699B2

(12) United States Patent
Jackson et al.

(10) Patent No.: US 9,039,699 B2
(45) Date of Patent: May 26, 2015

(54) METHODS AND SYSTEMS FOR TREATMENT OF TISSUE IN A BODY LUMEN

(75) Inventors: Jerome Jackson, Los Altos, CA (US); Roger A. Stern, Cupertino, CA (US)

(73) Assignee: Covidien LP, Mansfield, MA (US)

( * ) Notice: Subject to any disclaimer, the term of this patent is extended or adjusted under 35 U.S.C. 154(b) by 166 days.

(21) Appl. No.: 13/181,484

(22) Filed: Jul. 12, 2011

(65) Prior Publication Data

US 2012/0004656 A1 Jan. 5, 2012

Related U.S. Application Data

(60) Continuation-in-part of application No. 11/633,938, filed on Dec. 4, 2006, now Pat. No. 7,993,336, which is a division of application No. 10/754,452, filed on Jan. 9, 2004, now abandoned, which is a
(Continued)

(51) Int. Cl.
*A61B 18/14* (2006.01)
*A61B 5/107* (2006.01)
(Continued)

(52) U.S. Cl.
CPC .............. *A61B 5/1076* (2013.01); *A61B 5/037* (2013.01); *A61B 5/4233* (2013.01); *A61B 5/6885* (2013.01);
(Continued)

(58) Field of Classification Search
CPC .... A61B 18/12; A61B 18/14; A61B 18/1492; A61B 2018/0016; A61B 2018/00214; A61B 2018/00226; A61B 2018/0025; A61B 2018/00255; A61B 2018/00488; A61B 2018/00494; A61B 2018/1465; A61B 2018/1467

USPC .......... 606/32, 34, 41, 46–47, 49–50; 607/96, 607/98, 115–116, 133

See application file for complete search history.

(56) References Cited

U.S. PATENT DOCUMENTS 552,832 A 1/1896 Fort
3,901,241 A 8/1975 Allen, Jr.
(Continued)

FOREIGN PATENT DOCUMENTS

DE 3838840 5/1990
DE 4303882 8/1994
(Continued)

OTHER PUBLICATIONS

Castell, D.O. Gastroesophageal Reflux Disease: Current Strategies for Patient Management. Arch Fam Med. 1996; 5(4):221-227.
(Continued)

*Primary Examiner* — Ronald Hupczey, Jr.

(57) ABSTRACT

A system for measuring physiologic characteristics or treating tissue in a body lumen. The system may be used for treating abnormal mucosa in the esophagus. The system comprises an energy delivery device, such as an ablation device including an electrode support and an electrode pattern on the support. The ablation device may expand in size from a predeployed state to a deployed state. The system may include a sizing device having an inflatable balloon on a distal end of a catheter that is inflated with an expansion medium to expand the balloon to engage the wall of the esophagus so that the internal cross-section can be calculated or measured. The sizing device may also a controller for delivering an expansion medium and measuring the amount and pressure of the expansion medium inside the catheter. Methods of treating or diagnosing tissue are also disclosed.

18 Claims, 9 Drawing Sheets

Related U.S. Application Data continuation-in-part of application No. 10/370,645, filed on Feb. 19, 2003, now Pat. No. 7,530,979, which is a division of application No. 09/714,344, filed on Nov. 16, 2000, now Pat. No. 6,551,310.

(60) Provisional application No. 60/165,687, filed on Nov. 16, 1999.

(51) Int. Cl.

| | | |
|---|---|---|
| *A61B 5/03* | (2006.01) | |
| *A61B 5/00* | (2006.01) | |
| *A61N 1/06* | (2006.01) | |
| *A61B 18/00* | (2006.01) | |
| *A61B 19/00* | (2006.01) | |
| *A61N 1/08* | (2006.01) | |

(52) U.S. Cl.
CPC ..... *A61B 18/1492* (2013.01); *A61B 2018/0016* (2013.01); *A61B 2018/00214* (2013.01); *A61B 2018/0022* (2013.01); *A61B 2018/00488* (2013.01); *A61B 2018/00494* (2013.01); *A61B 2018/00577* (2013.01); *A61B 2018/00738* (2013.01); *A61B 2018/00797* (2013.01); *A61B 2019/461* (2013.01); *A61B 2019/464* (2013.01); *A61N 1/06* (2013.01); *A61N 1/08* (2013.01)

(56) References Cited

U.S. PATENT DOCUMENTS

| | | | |
|---|---|---|---|
| 3,924,628 A | | 12/1975 | Droegemueller et al. |
| 4,011,872 A | | 3/1977 | Komiya |
| 4,304,239 A | | 12/1981 | Perlin |
| 4,311,154 A | | 1/1982 | Sterzer et al. |
| 4,407,298 A | | 10/1983 | Lentz et al. |
| 4,411,266 A | | 10/1983 | Cosman |
| 4,532,924 A | | 8/1985 | Auth et al. |
| 4,565,200 A | | 1/1986 | Cosman |
| 4,640,298 A | * | 2/1987 | Pless et al. .................... 607/124 |
| 4,658,836 A | | 4/1987 | Turner |
| 4,662,383 A | | 5/1987 | Sogawa et al. |
| 4,674,481 A | | 6/1987 | Boddie, Jr. et al. |
| 4,676,258 A | | 6/1987 | Inokuchi et al. |
| 4,709,698 A | | 12/1987 | Johnston et al. |
| 4,765,331 A | | 8/1988 | Petruzzi et al. |
| 4,776,349 A | | 10/1988 | Nashef et al. |
| 4,860,744 A | | 8/1989 | Johnson et al. |
| 4,887,614 A | | 12/1989 | Shirakami et al. |
| 4,895,138 A | | 1/1990 | Yabe |
| 4,907,589 A | | 3/1990 | Cosman |
| 4,930,521 A | | 6/1990 | Metzger et al. |
| 4,943,290 A | | 7/1990 | Rexroth et al. |
| 4,947,842 A | | 8/1990 | Marchosky et al. |
| 4,949,147 A | | 8/1990 | Bacuvier |
| 4,955,377 A | | 9/1990 | Lennox et al. |
| 4,966,597 A | | 10/1990 | Cosman |
| 4,969,890 A | | 11/1990 | Sugita et al. |
| 4,976,711 A | | 12/1990 | Parins et al. |
| 4,979,948 A | | 12/1990 | Geddes et al. |
| 4,998,539 A | | 3/1991 | Delsanti |
| 5,006,119 A | | 4/1991 | Acker et al. |
| 5,010,895 A | | 4/1991 | Maurer et al. |
| 5,019,075 A | | 5/1991 | Spears et al. |
| 5,035,696 A | | 7/1991 | Rydell |
| 5,045,056 A | | 9/1991 | Behl |
| 5,046,512 A | | 9/1991 | Murchie |
| 5,047,028 A | | 9/1991 | Qian |
| 5,056,532 A | | 10/1991 | Hull et al. |
| 5,057,107 A | | 10/1991 | Parins et al. |
| 5,078,717 A | * | 1/1992 | Parins et al. .................... 606/48 |
| 5,083,565 A | | 1/1992 | Parins |
| 5,084,044 A | | 1/1992 | Quint |
| 5,088,979 A | | 2/1992 | Filipi et al. |
| 5,100,423 A | | 3/1992 | Fearnot |
| 5,106,360 A | | 4/1992 | Ishiwara et al. |
| 5,117,828 A | | 6/1992 | Metzger et al. |
| 5,122,137 A | | 6/1992 | Lennox |
| 5,125,928 A | | 6/1992 | Parins et al. |
| 5,151,100 A | | 9/1992 | Abele et al. |
| 5,156,151 A | * | 10/1992 | Imran .......................... 600/375 |
| 5,163,938 A | | 11/1992 | Kambara et al. |
| 5,171,299 A | | 12/1992 | Heitzmann et al. |
| 5,190,541 A | | 3/1993 | Abele et al. |
| 5,197,963 A | | 3/1993 | Parins |
| 5,197,964 A | | 3/1993 | Parins |
| 5,215,103 A | | 6/1993 | Desai |
| 5,236,413 A | | 8/1993 | Fiering |
| 5,242,441 A | | 9/1993 | Avitall |
| 5,255,679 A | | 10/1993 | Imran |
| 5,256,138 A | | 10/1993 | Vurek et al. |
| 5,257,451 A | | 11/1993 | Edwards et al. |
| 5,263,493 A | * | 11/1993 | Avitall .......................... 607/122 |
| 5,275,162 A | | 1/1994 | Edwards et al. |
| 5,275,169 A | | 1/1994 | Afromowitz et al. |
| 5,277,201 A | | 1/1994 | Stern |
| 5,281,216 A | | 1/1994 | Klicek |
| 5,281,217 A | | 1/1994 | Edwards et al. |
| 5,281,218 A | | 1/1994 | Imran |
| 5,290,286 A | | 3/1994 | Parins |
| 5,292,321 A | | 3/1994 | Lee |
| 5,293,869 A | * | 3/1994 | Edwards et al. ............... 600/375 |
| 5,309,910 A | | 5/1994 | Edwards et al. |
| 5,313,943 A | | 5/1994 | Houser et al. |
| 5,314,438 A | | 5/1994 | Shturman |
| 5,314,466 A | | 5/1994 | Stern et al. |
| 5,316,020 A | | 5/1994 | Truffer |
| 5,324,284 A | | 6/1994 | Imran |
| 5,328,467 A | | 7/1994 | Edwards et al. |
| 5,336,222 A | | 8/1994 | Durgin, Jr. et al. |
| 5,345,936 A | | 9/1994 | Pomeranz et al. |
| 5,348,554 A | | 9/1994 | Imran et al. |
| 5,363,861 A | | 11/1994 | Edwards et al. |
| 5,365,926 A | | 11/1994 | Desai |
| 5,366,490 A | | 11/1994 | Edwards et al. |
| 5,368,557 A | | 11/1994 | Nita et al. |
| 5,368,592 A | | 11/1994 | Stern et al. |
| 5,370,675 A | | 12/1994 | Edwards et al. |
| 5,370,678 A | | 12/1994 | Edwards et al. |
| 5,375,594 A | | 12/1994 | Cueva |
| 5,383,874 A | | 1/1995 | Jackson et al. |
| 5,383,876 A | | 1/1995 | Nardella |
| 5,383,917 A | | 1/1995 | Desai et al. |
| 5,385,544 A | | 1/1995 | Edwards et al. |
| 5,397,339 A | | 3/1995 | Desai |
| 5,398,683 A | | 3/1995 | Edwards et al. |
| 5,401,272 A | | 3/1995 | Perkins |
| 5,403,311 A | | 4/1995 | Abele et al. |
| 5,409,453 A | | 4/1995 | Lundquist et al. |
| 5,409,483 A | | 4/1995 | Campbell et al. |
| 5,411,025 A | | 5/1995 | Webster, Jr. |
| 5,413,573 A | | 5/1995 | Koivukangas |
| 5,415,657 A | | 5/1995 | Taymor-Luia |
| 5,421,819 A | | 6/1995 | Edwards et al. |
| 5,423,808 A | | 6/1995 | Edwards et al. |
| 5,423,811 A | | 6/1995 | Imran et al. |
| 5,423,812 A | | 6/1995 | Ellman et al. |
| 5,425,704 A | | 6/1995 | Sakurai et al. |
| 5,428,658 A | | 6/1995 | Oettinger et al. |
| 5,433,739 A | | 7/1995 | Sluijter et al. |
| 5,435,805 A | | 7/1995 | Edwards |
| 5,441,499 A | | 8/1995 | Fritzsch |
| 5,443,470 A | | 8/1995 | Stern et al. |
| 5,454,782 A | | 10/1995 | Perkins |
| 5,454,809 A | | 10/1995 | Janssen |
| 5,456,662 A | | 10/1995 | Edwards et al. |
| 5,456,682 A | | 10/1995 | Edwards et al. |
| 5,458,571 A | | 10/1995 | Lampropoulos et al. |
| 5,458,596 A | | 10/1995 | Lax et al. |
| 5,458,597 A | | 10/1995 | Edwards et al. |
| 5,462,545 A | | 10/1995 | Wang et al. |
| 5,465,717 A | | 11/1995 | Imran et al. |
| 5,470,308 A | | 11/1995 | Edwards et al. |

(56) References Cited

U.S. PATENT DOCUMENTS

| | | | |
|---|---|---|---|
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,490,984 A | 2/1996 | Freed | |
| 5,496,271 A | 3/1996 | Burton et al. | |
| 5,496,311 A | 3/1996 | Abele et al. | |
| 5,500,012 A | 3/1996 | Brucker et al. | |
| 5,505,728 A | 4/1996 | Ellman et al. | |
| 5,505,730 A | 4/1996 | Edwards | |
| 5,507,107 A * | 4/1996 | Pinomaki | 37/403 |
| 5,507,743 A | 4/1996 | Edwards et al. | |
| 5,509,419 A | 4/1996 | Edwards et al. | |
| 5,514,130 A | 5/1996 | Baker | |
| 5,514,131 A | 5/1996 | Edwards et al. | |
| 5,517,989 A | 5/1996 | Frisbie et al. | |
| 5,520,684 A | 5/1996 | Imran | |
| 5,522,815 A | 6/1996 | Burgin, Jr. et al. | |
| 5,524,622 A | 6/1996 | Wilson | |
| 5,531,676 A | 7/1996 | Edwards et al. | |
| 5,531,677 A | 7/1996 | Lundquist et al. | |
| 5,533,958 A | 7/1996 | Wilk | |
| 5,536,240 A | 7/1996 | Edwards et al. | |
| 5,536,267 A | 7/1996 | Edwards et al. | |
| 5,540,655 A | 7/1996 | Edwards et al. | |
| 5,542,916 A | 8/1996 | Hirsch et al. | |
| 5,542,928 A | 8/1996 | Evans et al. | |
| 5,549,644 A | 8/1996 | Lundquist et al. | |
| 5,549,661 A | 8/1996 | Korkis et al. | |
| RE35,330 E | 9/1996 | Malone et al. | |
| 5,554,110 A | 9/1996 | Edwards et al. | |
| 5,556,377 A | 9/1996 | Rosen et al. | |
| 5,558,672 A | 9/1996 | Edwards et al. | |
| 5,558,673 A | 9/1996 | Edwards et al. | |
| 5,562,720 A * | 10/1996 | Stern et al. | 607/98 |
| 5,566,221 A | 10/1996 | Smith et al. | |
| 5,569,241 A | 10/1996 | Edwards | |
| 5,571,116 A | 11/1996 | Bolanos et al. | |
| 5,578,007 A | 11/1996 | Imran | |
| 5,588,432 A | 12/1996 | Crowley | |
| 5,588,960 A | 12/1996 | Edwards et al. | |
| 5,591,195 A | 1/1997 | Taheri et al. | |
| 5,599,345 A | 2/1997 | Edwards et al. | |
| 5,609,151 A | 3/1997 | Mulier et al. | |
| 5,620,480 A | 4/1997 | Rudie | |
| 5,621,780 A | 4/1997 | Smith et al. | |
| 5,624,439 A | 4/1997 | Edwards et al. | |
| 5,651,780 A | 7/1997 | Jackson et al. | |
| 5,651,788 A | 7/1997 | Fleischer et al. | |
| 5,658,278 A | 8/1997 | Imran et al. | |
| 5,672,153 A | 9/1997 | Lax et al. | |
| 5,676,674 A | 10/1997 | Bolanos et al. | |
| 5,688,266 A | 11/1997 | Edwards et al. | |
| 5,688,490 A | 11/1997 | Tournier et al. | |
| 5,702,438 A | 12/1997 | Avitall | |
| 5,709,224 A | 1/1998 | Behl et al. | |
| 5,713,942 A | 2/1998 | Stern et al. | |
| 5,716,410 A | 2/1998 | Wang et al. | |
| 5,720,293 A | 2/1998 | Quinn et al. | |
| 5,730,128 A | 3/1998 | Pomeranz et al. | |
| 5,732,698 A | 3/1998 | Swanson et al. | |
| 5,738,096 A | 4/1998 | Ben-Haim | |
| 5,748,699 A | 5/1998 | Smith | |
| 5,769,846 A | 6/1998 | Edwards et al. | |
| 5,769,880 A | 6/1998 | Truckai et al. | |
| 5,779,698 A | 7/1998 | Clayman et al. | |
| 5,797,835 A | 8/1998 | Green | |
| 5,797,903 A | 8/1998 | Swanson et al. | |
| 5,800,334 A | 9/1998 | Wilk | |
| 5,800,429 A | 9/1998 | Edwards | |
| 5,807,261 A | 9/1998 | Benaron et al. | |
| 5,820,629 A | 10/1998 | Cox | |
| 5,823,197 A | 10/1998 | Edwards | |
| 5,823,955 A | 10/1998 | Kuck et al. | |
| 5,827,268 A * | 10/1998 | Laufer | 606/28 |
| 5,827,273 A | 10/1998 | Edwards | |
| 5,830,129 A | 11/1998 | Baer et al. | |
| 5,830,213 A | 11/1998 | Panescu et al. | |
| 5,833,688 A | 11/1998 | Sieben et al. | |
| 5,836,874 A * | 11/1998 | Swanson et al. | 600/374 |
| 5,842,984 A | 12/1998 | Avitall | |
| 5,846,196 A | 12/1998 | Siekmeyer et al. | |
| 5,860,974 A | 1/1999 | Abele | |
| 5,861,036 A | 1/1999 | Godin | |
| 5,863,291 A | 1/1999 | Schaer | |
| 5,871,483 A | 2/1999 | Jackson et al. | |
| 5,876,340 A | 3/1999 | Tu et al. | |
| 5,888,743 A | 3/1999 | Das | |
| 5,891,134 A | 4/1999 | Goble et al. | |
| 5,895,355 A | 4/1999 | Schaer | |
| 5,902,263 A | 5/1999 | Patterson et al. | |
| 5,904,711 A | 5/1999 | Flom et al. | |
| 5,925,044 A | 7/1999 | Hofmann et al. | |
| 5,938,694 A | 8/1999 | Jaraczewski et al. | |
| 5,964,755 A | 10/1999 | Edwards | |
| 5,976,129 A | 11/1999 | Desai | |
| 5,984,861 A | 11/1999 | Crowley | |
| 5,997,534 A | 12/1999 | Tu et al. | |
| 6,006,755 A | 12/1999 | Edwards | |
| 6,009,877 A * | 1/2000 | Edwards | 128/898 |
| 6,010,511 A | 1/2000 | Murphy | |
| 6,012,457 A * | 1/2000 | Lesh | 128/898 |
| 6,016,437 A | 1/2000 | Tu et al. | |
| 6,023,638 A | 2/2000 | Swanson et al. | |
| 6,027,499 A | 2/2000 | Johnston et al. | |
| 6,033,397 A | 3/2000 | Laufer et al. | |
| 6,039,701 A | 3/2000 | Sliwa et al. | |
| 6,041,260 A | 3/2000 | Stern et al. | |
| 6,044,846 A | 4/2000 | Edwards | |
| 6,053,172 A | 4/2000 | Hovda et al. | |
| 6,053,913 A | 4/2000 | Tu et al. | |
| 6,056,744 A | 5/2000 | Edwards | |
| 6,059,719 A | 5/2000 | Yamamoto et al. | |
| 6,068,629 A | 5/2000 | Haissaguerre et al. | |
| 6,071,277 A | 6/2000 | Farley et al. | |
| 6,073,052 A | 6/2000 | Zelickson et al. | |
| 6,086,558 A | 7/2000 | Bower et al. | |
| 6,091,993 A | 7/2000 | Bouchier et al. | |
| 6,091,995 A | 7/2000 | Ingle et al. | |
| 6,092,528 A | 7/2000 | Edwards | |
| 6,095,966 A | 8/2000 | Chornenky et al. | |
| 6,096,054 A | 8/2000 | Wyzgala et al. | |
| 6,102,908 A | 8/2000 | Tu et al. | |
| 6,112,123 A | 8/2000 | Kelleher et al. | |
| 6,120,434 A | 9/2000 | Kimura et al. | |
| 6,123,703 A | 9/2000 | Tu et al. | |
| 6,123,718 A * | 9/2000 | Tu et al. | 607/113 |
| 6,138,046 A | 10/2000 | Dalton | |
| 6,142,994 A | 11/2000 | Swanson et al. | |
| 6,146,149 A | 11/2000 | Daound | |
| 6,149,647 A | 11/2000 | Tu et al. | |
| 6,152,920 A * | 11/2000 | Thompson et al. | 606/41 |
| 6,162,237 A | 12/2000 | Chan | |
| 6,179,836 B1 | 1/2001 | Eggers et al. | |
| 6,182,666 B1 | 2/2001 | Dobak, III | |
| 6,183,468 B1 | 2/2001 | Swanson et al. | |
| 6,197,022 B1 | 3/2001 | Baker | |
| 6,237,355 B1 | 5/2001 | Li | |
| 6,238,392 B1 | 5/2001 | Long | |
| 6,245,065 B1 | 6/2001 | Panescu et al. | |
| 6,254,598 B1 | 7/2001 | Edwards et al. | |
| 6,254,599 B1 | 7/2001 | Lesh et al. | |
| 6,258,087 B1 | 7/2001 | Edwards et al. | |
| 6,273,886 B1 | 8/2001 | Edwards et al. | |
| 6,321,121 B1 | 11/2001 | Zelickson et al. | |
| 6,325,798 B1 | 12/2001 | Edwards et al. | |
| 6,325,800 B1 | 12/2001 | Durgin et al. | |
| 6,338,726 B1 | 1/2002 | Edwards et al. | |
| 6,355,031 B1 | 3/2002 | Edwards et al. | |
| 6,355,032 B1 | 3/2002 | Hovda et al. | |
| 6,358,245 B1 | 3/2002 | Edwards et al. | |
| 6,363,937 B1 | 4/2002 | Hovda et al. | |
| 6,383,181 B1 | 5/2002 | Johnston et al. | |
| 6,394,949 B1 | 5/2002 | Crowley et al. | |

(56) References Cited

U.S. PATENT DOCUMENTS

| | | |
|---|---|---|
| 6,402,744 B2 | 6/2002 | Edwards et al. |
| 6,405,732 B1 | 6/2002 | Edwards et al. |
| 6,409,723 B1 | 6/2002 | Edwards |
| H2037 H | 7/2002 | Yates et al. |
| 6,415,016 B1 | 7/2002 | Chornenky et al. |
| 6,416,511 B1 | 7/2002 | Lesh et al. |
| 6,423,058 B1 | 7/2002 | Edwards et al. |
| 6,425,877 B1 | 7/2002 | Edwards |
| 6,428,536 B2 | 8/2002 | Panescu et al. |
| 6,432,104 B1 | 8/2002 | Durgin et al. |
| 6,440,128 B1 | 8/2002 | Edwards et al. |
| 6,448,658 B2 | 9/2002 | Takata et al. |
| 6,451,014 B1 | 9/2002 | Wakikaido et al. |
| 6,454,790 B1 | 9/2002 | Neuberger et al. |
| 6,464,697 B1 | 10/2002 | Edwards et al. |
| 6,468,272 B1 | 10/2002 | Koblish et al. |
| 6,514,246 B1 | 2/2003 | Swanson et al. |
| 6,514,249 B1 | 2/2003 | Maguire et al. |
| 6,535,768 B1 | 3/2003 | Baker et al. |
| 6,544,226 B1 | 4/2003 | Gaiser et al. |
| 6,547,776 B1 | 4/2003 | Gaiser et al. |
| 6,547,787 B1 | 4/2003 | Altman et al. |
| 6,551,302 B1 | 4/2003 | Rosinko et al. |
| 6,551,310 B1 | 4/2003 | Ganz et al. |
| 6,551,315 B2 | 4/2003 | Kortenbach et al. |
| 6,562,034 B2 | 5/2003 | Edwards et al. |
| 6,572,578 B1 | 6/2003 | Blanchard |
| 6,572,610 B2 | 6/2003 | Kovalcheck et al. |
| 6,572,639 B1 | 6/2003 | Ingle et al. |
| 6,575,966 B2 | 6/2003 | Lane et al. |
| 6,589,238 B2 | 7/2003 | Edwards et al. |
| 6,613,047 B2 | 9/2003 | Edwards |
| 6,641,581 B2 | 11/2003 | Muzzammel |
| 6,663,626 B2 | 12/2003 | Truckai et al. |
| 6,673,070 B2 | 1/2004 | Edwards et al. |
| 6,682,528 B2 | 1/2004 | Frazier et al. |
| 6,689,130 B2 | 2/2004 | Arail et al. |
| 6,695,764 B2 | 2/2004 | Silverman et al. |
| 6,712,074 B2 | 3/2004 | Edwards et al. |
| 6,712,814 B2 | 3/2004 | Edwards et al. |
| 6,712,815 B2 | 3/2004 | Sampson et al. |
| 6,740,082 B2 | 5/2004 | Shadduck |
| 6,749,607 B2 | 6/2004 | Edwards et al. |
| 6,752,806 B2 | 6/2004 | Durgin et al. |
| 6,800,083 B2 | 10/2004 | Hiblar et al. |
| 6,837,886 B2 | 1/2005 | Collins et al. |
| 6,846,312 B2 | 1/2005 | Edwards et al. |
| 6,860,878 B2 | 3/2005 | Brock |
| 6,866,663 B2 | 3/2005 | Edwards et al. |
| 6,872,206 B2 | 3/2005 | Edwards et al. |
| 6,917,834 B2 | 7/2005 | Koblish et al. |
| 6,918,906 B2 | 7/2005 | Long |
| 6,923,808 B2 | 8/2005 | Taimisto |
| 6,929,642 B2 | 8/2005 | Xiao et al. |
| 6,953,469 B2 | 10/2005 | Ryan |
| 6,964,661 B2 | 11/2005 | Rioux et al. |
| 6,971,395 B2 | 12/2005 | Edwards et al. |
| 6,974,456 B2 | 12/2005 | Edwards et al. |
| 6,994,704 B2 | 2/2006 | Qin et al. |
| 7,004,938 B2 | 2/2006 | Ormsby et al. |
| 7,048,734 B1 | 5/2006 | Fleischman et al. |
| 7,056,320 B2 | 6/2006 | Utley et al. |
| 7,083,620 B2 | 8/2006 | Jahns et al. |
| 7,089,063 B2 | 8/2006 | Lesh et al. |
| 7,122,031 B2 | 10/2006 | Edwards et al. |
| 7,125,407 B2 | 10/2006 | Edwards et al. |
| 7,150,745 B2 | 12/2006 | Stern et al. |
| 7,160,294 B2 | 1/2007 | Croft |
| 7,165,551 B2 | 1/2007 | Edwards |
| 7,167,758 B2 | 1/2007 | Baker et al. |
| 7,179,257 B2 | 2/2007 | West et al. |
| 7,184,827 B1 | 2/2007 | Edwards |
| 7,293,563 B2 | 11/2007 | Utley et al. |
| 7,326,207 B2 | 2/2008 | Edwards |
| 7,329,254 B2 | 2/2008 | West et al. |
| 7,344,535 B2 | 3/2008 | Stern et al. |
| 7,416,549 B2 | 8/2008 | Young et al. |
| 7,425,212 B1 | 9/2008 | Danek et al. |
| 7,507,234 B2 | 3/2009 | Utley et al. |
| 7,507,238 B2 | 3/2009 | Utley et al. |
| 7,507,239 B2 | 3/2009 | Shadduck |
| 7,530,979 B2 | 5/2009 | Ganz et al. |
| 7,556,628 B2 | 7/2009 | Utley et al. |
| 7,632,268 B2 | 12/2009 | Utley et al. |
| 7,680,543 B2 | 3/2010 | Azure |
| 7,727,191 B2 | 6/2010 | Mihalik et al. |
| 7,850,685 B2 | 12/2010 | Kunis et al. |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,377,055 B2 | 2/2013 | Jackson |
| 2001/0041887 A1 | 11/2001 | Crowley |
| 2001/0044625 A1 | 11/2001 | Hata et al. |
| 2001/0051802 A1 | 12/2001 | Woloszko et al. |
| 2002/0087151 A1 | 7/2002 | Mody et al. |
| 2002/0128650 A1 | 9/2002 | McClurken |
| 2002/0177847 A1 | 11/2002 | Long |
| 2002/0183739 A1 | 12/2002 | Long |
| 2003/0069572 A1 | 4/2003 | Wellman et al. |
| 2003/0093117 A1 | 5/2003 | Saadat |
| 2003/0109837 A1 | 6/2003 | McBride-Sakal |
| 2003/0153905 A1 | 8/2003 | Edwards et al. |
| 2003/0158550 A1 | 8/2003 | Ganz et al. |
| 2003/0181900 A1 | 9/2003 | Long |
| 2003/0181905 A1 | 9/2003 | Long |
| 2003/0191512 A1 | 10/2003 | Laufer et al. |
| 2003/0216727 A1 | 11/2003 | Long |
| 2004/0087936 A1 | 5/2004 | Stern et al. |
| 2004/0122452 A1 | 6/2004 | Deem et al. |
| 2004/0147916 A1 | 7/2004 | Baker |
| 2004/0153120 A1 | 8/2004 | Seifert et al. |
| 2004/0172016 A1 | 9/2004 | Bek et al. |
| 2004/0204708 A1 | 10/2004 | Edwards et al. |
| 2004/0215180 A1 | 10/2004 | Starkebaum et al. |
| 2004/0215235 A1 | 10/2004 | Jackson et al. |
| 2004/0215296 A1 | 10/2004 | Ganz et al. |
| 2004/0236316 A1 | 11/2004 | Danitz et al. |
| 2004/0243124 A1 | 12/2004 | Im et al. |
| 2005/0010162 A1 | 1/2005 | Utley et al. |
| 2005/0033271 A1 | 2/2005 | Qin et al. |
| 2005/0070978 A1 | 3/2005 | Bek et al. |
| 2005/0090817 A1 | 4/2005 | Phan |
| 2005/0096713 A1 | 5/2005 | Starkebaum et al. |
| 2005/0107829 A1 | 5/2005 | Edwards et al. |
| 2005/0143727 A1 | 6/2005 | Koblish et al. |
| 2005/0149013 A1 | 7/2005 | Lee |
| 2005/0154386 A1 | 7/2005 | West et al. |
| 2005/0159743 A1 | 7/2005 | Edwards et al. |
| 2005/0187546 A1 | 8/2005 | Bek et al. |
| 2005/0215983 A1 | 9/2005 | Brock |
| 2005/0245926 A1 | 11/2005 | Edwards et al. |
| 2005/0288664 A1 | 12/2005 | Ford et al. |
| 2006/0009758 A1 | 1/2006 | Edwards et al. |
| 2006/0015162 A1 | 1/2006 | Edward et al. |
| 2006/0020276 A1 | 1/2006 | Saadat et al. |
| 2006/0041256 A1 | 2/2006 | Edwards et al. |
| 2006/0069303 A1 | 3/2006 | Couvillon |
| 2006/0086363 A1 | 4/2006 | Qin et al. |
| 2006/0095032 A1 | 5/2006 | Jackson et al. |
| 2006/0247614 A1 | 11/2006 | Sampson |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0282071 A1 | 12/2006 | Utley et al. |
| 2007/0066973 A1 | 3/2007 | Stern et al. |
| 2007/0100333 A1 | 5/2007 | Jackson et al. |
| 2007/0118104 A1 | 5/2007 | Wallace et al. |
| 2007/0118106 A1 | 5/2007 | Utley et al. |
| 2007/0118159 A1 | 5/2007 | Deem et al. |
| 2007/0135809 A1 | 6/2007 | Utley et al. |
| 2007/0142831 A1 | 6/2007 | Shadduck |
| 2007/0167963 A1 | 7/2007 | Deem et al. |
| 2007/0219570 A1 | 9/2007 | Deem et al. |

(56) References Cited

U.S. PATENT DOCUMENTS

| | | |
|---|---|---|
| 2007/0255296 A1 | 11/2007 | Sauer |
| 2007/0287994 A1 | 12/2007 | Patel |
| 2007/0288001 A1 | 12/2007 | Patel |
| 2007/0299433 A1 | 12/2007 | Williams et al. |
| 2008/0097427 A1 | 4/2008 | Stern et al. |
| 2008/0275445 A1 | 11/2008 | Kelly et al. |
| 2008/0319350 A1 | 12/2008 | Wallace et al. |
| 2009/0012512 A1 | 1/2009 | Utley et al. |
| 2009/0012513 A1 | 1/2009 | Utley et al. |
| 2009/0012518 A1 | 1/2009 | Utley et al. |
| 2009/0036733 A1 | 2/2009 | Wallace et al. |
| 2009/0036886 A1 | 2/2009 | Utley et al. |
| 2009/0048593 A1 | 2/2009 | Ganz et al. |
| 2009/0177194 A1 | 7/2009 | Wallace et al. |
| 2009/0187181 A1 | 7/2009 | Shadduck |
| 2009/0299355 A1 | 12/2009 | Bencini et al. |
| 2009/0318914 A1 | 12/2009 | Utley |
| 2010/0063495 A1 | 3/2010 | Edwards et al. |
| 2010/0130970 A1 | 5/2010 | Williams et al. |
| 2010/0191237 A1 | 7/2010 | Shadduck |
| 2010/0204560 A1 | 8/2010 | Salahieh et al. |
| 2010/0234840 A1 | 9/2010 | Jackson et al. |
| 2012/0004656 A1 | 1/2012 | Jackson |

FOREIGN PATENT DOCUMENTS

| | | |
|---|---|---|
| EP | 0105677 A1 | 4/1984 |
| EP | 0115420 A2 | 8/1984 |
| EP | 0139607 B1 | 5/1985 |
| EP | 0251745 A1 | 1/1988 |
| EP | 0521595 A2 | 1/1993 |
| EP | 0608609 B1 | 8/1994 |
| EP | 1323382 A1 | 7/2003 |
| EP | 1634542 B1 | 3/2006 |
| JP | 7-184919 | 7/1995 |
| JP | 8-506738 | 7/1996 |
| JP | 8-509875 | 10/1996 |
| JP | 2003510160 | 3/2003 |
| JP | 2005503181 | 2/2005 |
| WO | WO 91/01773 A1 | 2/1991 |
| WO | WO 91/03207 A1 | 3/1991 |
| WO | WO 92/10142 A1 | 6/1992 |
| WO | WO 93/08755 A1 | 5/1993 |
| WO | WO 94/07446 A1 | 4/1994 |
| WO | WO 94/10925 A1 | 5/1994 |
| WO | WO 94/21165 A1 | 9/1994 |
| WO | WO 94/22366 A1 | 10/1994 |
| WO | WO 94/26178 A1 | 11/1994 |
| WO | WO 95/18575 A1 | 7/1995 |
| WO | WO 95/19142 A1 | 7/1995 |
| WO | WO 95/25472 A1 | 9/1995 |
| WO | WO 96/00042 A1 | 1/1996 |
| WO | WO 96/16606 A1 | 6/1996 |
| WO | WO 96/29946 A1 | 10/1996 |
| WO | WO 97/04702 A1 | 2/1997 |
| WO | WO 97/06857 A2 | 2/1997 |
| WO | WO 97/32532 A1 | 9/1997 |
| WO | WO 97/43971 A1 | 11/1997 |
| WO | WO 98/12999 A2 | 4/1998 |
| WO | WO 98/14238 A1 | 4/1998 |
| WO | WO 98/18393 A1 | 5/1998 |
| WO | WO 99/03413 A1 | 1/1999 |
| WO | WO 99/35987 A1 | 7/1999 |
| WO | WO 99/42046 A1 | 8/1999 |
| WO | WO 99/55245 A1 | 11/1999 |
| WO | WO 00/01313 A1 | 1/2000 |
| WO | 0062699 | 10/2000 |
| WO | WO 00/59393 A1 | 10/2000 |
| WO | WO 00/62699 A2 | 10/2000 |
| WO | 0066017 | 11/2000 |
| WO | 0066020 | 11/2000 |
| WO | 0066021 | 11/2000 |
| WO | 0066052 | 11/2000 |
| WO | 0069376 | 11/2000 |
| WO | WO 00/66017 A1 | 11/2000 |
| WO | WO 00/66021 A1 | 11/2000 |
| WO | WO 00/69376 A1 | 11/2000 |
| WO | 0122897 | 4/2001 |
| WO | WO 01/22897 A1 | 4/2001 |
| WO | 0135846 | 5/2001 |
| WO | WO 01/35846 A1 | 5/2001 |
| WO | WO 01/45550 A2 | 6/2001 |
| WO | WO 01/89440 A2 | 11/2001 |
| WO | WO 02/096327 A2 | 12/2002 |
| WO | WO 03/070091 A1 | 8/2003 |
| WO | WO 03/092609 A2 | 11/2003 |
| WO | WO 2007/001981 A2 | 1/2007 |
| WO | 2007061984 | 5/2007 |

OTHER PUBLICATIONS

Dallamagne et al; Laparoscopic Nissen Fundoplication: Preliminary. Surgical Laparoscopy and Endoscopy. 1991; 1(3):138-143.

Hinder et al; The Technique of Laparoscopic Nissen Fundoplication. Surgical Laparoscopy and Endoscopy. 1992; 2(3):265-272.

Kaneko et al; Physiological Laryngeal Pacemaker. Trans Am Soc. Artif Intern Organs. 1985; XXXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K.A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22sul3):S5-S12.

Rice et al; Endoscopic Paranasal Sinus Surgery. Chapter 5, Functional Endoscopic Paranasal Sinus Surgery, The Technique of Messerklinger. Raven Press. 1988; 75-102.

Rice et al; Endoscopic Paranasal Sinus Surgery. Chapter 6, Total Endoscopic Sphenoethmoidectomy. The Technique of Wigand. Raven Press. 1988; 103-125.

Rodriguez et al.(ASGE Technology Committee); Technology Status Evaluation Report,; Mucosal ablation devices; Gastoinestinal Endoscopy; vol. 68; No. 6; pp. 1031-1042; Dec. 2008.

Salameh et al; An Animal Model Study to Clarify and Investigate Endoscopic Tissue Coagulation by Using a New Monopolar Device. Gastrointestinal Endoscopy; 2004; 59 (1): 107-112.

Urshel, J.D. Complications of Antireflux Surgery. Am J. Surg. 1993; 166 (1):68-70.

Wallace et al.; U.S. Appl. No. 13/051,738 entitled "Selectively expandable operative element support structure and methods of use," filed Mar. 18, 2011.

Utley et al.; U.S. Appl. No. 13/181,490 entitled "Precision ablating method," filed Jul. 12, 2011.

Jackson et al.; U.S. Appl. No. 13/189,793 entitled "Methods and systems for determining physiologic characteristics for treatment of the esophagus," filed Jul. 25, 2011.

* cited by examiner

FIG. 7

Diameter Estimation Algorithm

| | Object Diameter (mm) | Diameter Measuring Probe Inflation Volume (cm3) | ((((h/6)+(L/4))*pi) | d^2 | d(cm) | Circular Diameter Calculation (mm) | Difference | Percent Error | Corrected Diameter Estimate (mm) (1.104 factor) |
|---|---|---|---|---|---|---|---|---|---|
| 20cc syringe | 19.05 | 13 | 3.816930354 | 3.40588 | 1.845502162 | 0.18455 | | | |
| 19 mm tubing - 1 | 19.05 | 16.5 | 3.816930354 | 4.32285 | 2.079145364 | 20.79145 | 1.741454 | 9.141489 | 18.83283844 |
| 16 mm tubing | 15.875 | 11.5 | 3.816930354 | 3.01289 | 1.735768499 | 17.35768 | 1.482685 | 9.339748 | 15.72254075 |
| Pig Esophagus | 34 | 40 | 3.816930354 | 10.4796 | 3.237224942 | 32.37225 | -1.62775 | -4.7875 | 29.32268969 |
| 25 mm tubing | 25.4 | 32 | 3.816930354 | 8.3837 | 2.895462011 | 28.95462 | 3.55462 | 13.99457 | 26.22701097 |
| 19 mm tubing -2 | 19.05 | 16.5 | 3.816930354 | 4.32285 | 2.079145364 | 20.79145 | 1.741454 | 9.141489 | 18.83283844 |

METHODS AND SYSTEMS FOR TREATMENT OF TISSUE IN A BODY LUMEN

CROSS REFERENCE TO RELATED APPLICATIONS

This application is a continuation-in-part of U.S. patent application Ser. No. 11/633,938 filed Dec. 4, 2006, now U.S. Pat. No. 7,993,336, which is a divisional of U.S. patent application Ser. No. 10/754,452 filed Jan. 9, 2004, now abandoned, which is a continuation-in-part of U.S. patent application Ser. No. 10/370,645, filed Feb. 19, 2003, now U.S. Pat. No. 7,530,979, which is a divisional of U.S. patent application Ser. No. 09/714,344 filed Nov. 16, 2000, now U.S. Pat. No. 6,551,310, which claims the benefit under 35 USC 119(e) of U.S. Provisional Application No. 60/165,687 filed Nov. 16, 1999, the full disclosure of which are fully incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

1. Field of the Invention

The present invention relates generally to medical methods and systems. More particularly, the invention is directed to methods and systems for treating and determining physiologic characteristics of body lumens such as the esophagus.

The human body has a number of internal body lumens or cavities located within, many of which have an inner lining or layer. These inner linings can be susceptible to disease. In some cases, surgical intervention can be required to remove the inner lining in order to prevent the spread of disease to otherwise healthy tissue located nearby.

Those with persistent problems or inappropriate relaxation of the lower esophageal sphincter can develop a condition known as gastroesophageal reflux disease, manifested by classic symptoms of heartburn and regurgitation of gastric and intestinal content. The causative agent for such problems may vary. Patients with severe forms of gastroesophageal reflux disease, no matter what the cause, can sometimes develop secondary damage of the esophagus due to the interaction of gastric or intestinal contents with esophageal cells not designed to experience such interaction.

The esophagus is composed of three primary tissue layers; a superficial mucosal layer lined by squamous epithelial cells, a middle submucosal layer and a deeper muscle layer. When gastroesophageal reflux occurs, the superficial squamous epithelial cells are exposed to gastric acid, along with intestinal bile acids and enzymes. This exposure may be tolerated, but in some cases can lead to damage and alteration of the squamous cells, causing them to change into taller, specialized columnar epithelial cells. This metaplastic change of the mucosal epithelium from squamous cells to columnar cells is called Barrett's esophagus, named after the British surgeon who originally described the condition.

Barrett's esophagus has important clinical consequences, since the Barrett's columnar cells can, in some patients, become dysplastic and then progress to a certain type of deadly cancer of the esophagus. The presence of Barrett's esophagus is the main risk factor for the development of adenocarcinoma of the esophagus.

Accordingly, attention has been focused on identifying and removing this abnormal Barrett's columnar epithelium in order to mitigate more severe implications for the patient. Devices and methods for treating abnormal body tissue by application of various forms of energy to such tissue have been described, such as radio frequency ablation. However, without precise control of the depth of penetration of the energy means, these methods and devices are deficient. Uncontrolled energy application can penetrate too deeply into the esophageal wall, beyond the mucosa and submucosal layers, into the muscularis externa, potentially causing esophageal perforation, stricture or bleeding. Accordingly, proper administration of the correct amount of treatment energy to the tissue can be facilitated by knowledge of the size of the esophagus and area to be treated.

Additionally, medical procedures for treating Barrett's esophagus typically involve deployment of an expandable catheter inside the esophagus. Expandable catheters are preferred because the profile of the catheter is ideally as small as possible to allow for ease of delivery, while treatment of the esophagus is most efficiently performed when the catheter is at or slightly larger than the diameter of the esophageal wall. Proper sizing and/or pressurization of the delivery device is therefore desirable to prevent over-distension of the organ, which could result in harm to the organ, or under-expansion of the catheter, which often results in incomplete treatment. Accordingly, accurate and simple measurement of the size of the lumen and control of the pressure of the catheter on the lumen surface promotes the proper engagement and delivery of energy to the luminal wall so that a uniform and controlled depth of treatment can be administered. In addition to calculating luminal dimensions, the compliance of the lumen can be determined by measuring the cross section of the lumen at two or more pressure values.

Therefore, it would be advantageous to have methods and systems for accurately determining in vivo the size and optionally the compliance of a body lumen such as the esophagus. In addition, it would be desirable to provide a method and system for treating the body lumen once having determined its size. At least some of these objectives will be met by the present invention.

2. Description of the Background Art

U.S. Pat. No. 5,275,169 describes apparatus and methods for determining physiologic characteristics of blood vessels. The device measures the diameter and wall compliance of the blood vessel, and does not administer treatment. Additionally, the method relies on using only an incompressible fluid to inflate a balloon inside a blood vessel. Other patents of interest include U.S. Pat. Nos. 6,010,511; 6,039,701; and 6,551,310.

BRIEF SUMMARY OF THE INVENTION

The present invention comprises methods and systems for sizing a body lumen, such as the esophagus. Methods and systems are also provided for treating the body lumen once the proper measurements have been made.

Although the following description will focus on embodiments configured for treatment of the esophagus, other embodiments may be used to treat any other suitable lumen in the body. In particular, the methods and systems of the present invention may be used whenever accurate measurement of a body lumen or uniform delivery of energy is desired to treat a controlled depth of tissue in a lumen or cavity of the body, especially where such body structures may vary in size.

Therefore, the following description is provided for exemplary purposes and should not be construed to limit the scope of the invention.

In one aspect of the invention, a method for treating a body lumen at a treatment location comprises measuring a luminal dimension at the treatment location of the lumen, selecting an electrode deployment device having an array of electrodes or other electrode structure with a pre-selected deployed size which corresponds to the measured dimension, positioning the electrode deployment device at the treatment location within the lumen, deploying the electrode array to the pre-selected deployed state to engage a wall of the lumen, and delivering energy to the electrodes for treatment of the luminal tissue.

In some embodiments, measuring the luminal dimension comprises positioning a sizing member at the treatment location within the lumen, expanding the sizing member until it engages an inside wall of the lumen, and calculating the luminal dimension at the treatment location of the esophagus based on the expansion of the sizing member. Often, expanding the sizing member comprises inflating a sizing balloon by introducing an expansion medium. The expansion medium may be a compressible or non-compressible fluid. In some embodiments, the lumen dimensions are calculated by determining the amount of the expansion medium introduced to the sizing balloon while it is inflated. For example, the mass or volume of the expansion medium can be measured by use of a mass-flow meter or the like. Optionally, a pressure sensor may be coupled to the sizing balloon, so that the luminal dimension can be calculated from the measured amount of expansion medium introduced to the balloon at a given pressure. Alternatively, the sizing member may comprise a basket, plurality of struts, or calipers, or the like. The lumen may also be measured by ultrasound, optical, or fluoroscopic imaging or by use of measuring strip.

In embodiments where a sizing balloon is employed, the sizing balloon may comprise any material or configuration. In general, the sizing balloon is cylindrical and has a known length and a diameter that is greater than the diameter of the target lumen. In this configuration, the sizing balloon is non-distensible, such as a bladder having a diameter in its fully expanded form that is larger than the lumen diameter. Suitable materials for the balloon may comprise a polymer such as polyimide or polyethylene terephthalate (PET). Alternatively, the balloon may comprise an elastomer or mixture of polymers and elastomers.

Once the lumen dimensions are determined, an electrode deployment device matching the measured luminal dimension may be selected from an inventory of devices having different electrode deployment sizes. In some embodiments, the electrode deployment device is transesophageally delivered to a treatment area within the esophagus. For example, delivering the device may be facilitated by advancing a catheter through the esophagus, wherein the catheter carries the electrode array and an expansion member. The expansion member may comprise any of the materials or configurations of the sizing member, such as an inflatable cylindrical balloon comprising a polymer such as polyimide or PET.

In some aspects of the invention, the array of electrodes or other electrode structure are arranged on a surface of a dimensionally stable support such as a non-distensible, electrode backing. The backing may comprise a thin, rectangular sheet of polymer materials such as polyimide, polyester or other flexible thermoplastic or thermosetting polymer film, polymer covered materials, or other nonconductive materials. The backing may also comprise an electrically insulating polymer, with an electro-conductive material, such as copper, deposited onto a surface. For example, an electrode pattern can be etched into the material to create an array of electrodes. The electrode pattern may be aligned in an axial or traverse direction across the backing, formed in a linear or non-linear parallel array or series of bipolar pairs, or other suitable pattern. In many embodiments, delivering energy comprises applying radiofrequency (RF) energy to tissue of the body lumen through the electrodes. Depending on the desired treatment effect, the electrodes may be arranged to control the depth and pattern of treatment. For treatment of esophageal tissue, the electrode widths are less than 3 mm, typically a width in the range from 0.1 mm to 3 mm, preferably 0.1 mm to 0.3 mm, and adjacent electrodes are spaced apart less than 3 mm, typically in the range from 0.1 mm to 3 mm, preferably from 0.1 mm to 0.3 mm. Alternatively, energy may be delivered by use of structures other than those having an array of electrodes. For example, the electrode structure may comprise a continuous electrode arranged in a helical pattern over the balloon.

In another method of the present invention, the measurement of the luminal dimension may be used to determine the amount of energy delivered to the tissue of the lumen. For example, a method for treating the tissue of a body lumen at a treatment location comprises measuring a luminal dimension at a location of the lumen, positioning an electrode deployment device at that location, deploying the expansion member to engage an electrode array to a wall of the lumen; and delivering sufficient energy to the electrode array for treatment of the luminal tissue based on the measured dimension of the lumen. In general, the amount of power delivered to the electrodes will vary depending on the type of treatment and the overall surface area of the luminal tissue to be treated. In some embodiments, the expansion member can variably expand to engage the wall of the lumen independent of the size of the lumen. For esophageal treatment, the expansion member may comprise a balloon that can expand to a range of diameters between 12 mm and 50 mm. Typically, the total energy density delivered to the esophageal tissue will be in the range from 1 J/cm2 to 50 J/cm2, usually being from 5 J/cm2 to 15 J/cm2. In order to effectively ablate the mucosal lining of the esophagus and allow re-growth of a normal mucosal lining without creating damage to underlying tissue structures, it is preferable to deliver the radiofrequency energy over a short time span in order to reduce the effects of thermal conduction of energy to deeper tissue layers, thereby creating a "searing" effect. It is preferable to deliver the radiofrequency energy within a time span of less than 5 seconds. An optimal time for effective treatment is less than 1 second, and preferably less than 0.5 second or 0.25 seconds. The lower bound on time may be limited by the ability of the RF power source to deliver high powers.

In one aspect of the invention, a method for measuring an internal dimension at a location in a body lumen comprises positioning a cylindrical balloon at a location within the lumen, inflating the balloon with an expansion medium to engage an inside wall of the lumen, monitoring the extent of engagement of the balloon, determining the amount of expansion medium in the balloon while inflated at the location, and calculating the internal dimension of the esophagus based on the length of the balloon and the measured amount of expansion medium inside the balloon. In some embodiments, the balloon is transesophageally delivered to a treatment area within the esophagus by advancing a catheter carrying the balloon through the esophagus. Often, the balloon is non-distensible and has a diameter that is greater than the diameter of the inside wall of the lumen. The balloon may be filled with an expansion medium that is a compressible fluid, such as air.

Monitoring the extent of engagement comprises determining the expansion of the balloon via a pressure sensor coupled to the balloon, wherein the extent of engagement is determined by the internal pressure exerted from the expansion medium as measured by the pressure sensor and by visual verification. The pressure sensor may comprise any device for determining the pressure inside a vessel, such as a strain gauge. Alternatively, the extent of may be monitored by determining the expansion of the balloon via visual inspection. In some embodiments, the balloon may be expanded to apply pressure to the inside wall of the lumen, thereby causing the lumen to stretch.

In one aspect of the invention, a method for determining wall compliance of an esophagus comprises positioning a balloon at a location within the esophagus, inflating the balloon with a compressible fluid, measuring the static pressure within the balloon, measuring the total amount of fluid within the balloon at least two static pressure values, and calculating the wall compliance based on the variation in the amount of fluid between a first measured pressure and a second measured pressure. For esophageal treatment, the static pressure values to be used are typically below 10 psig, and preferably at or below 7 psig.

In another aspect, a system for treating tissue of a body lumen comprises a sizing member for measuring the cross section at a location of the lumen and a catheter having a set of individual treatment devices, each device comprising an electrode array adapted to treat a target location, wherein at least some of the arrays are adapted to treat locations having different sizes determined by the sizing member. In some embodiments, the sizing member comprises an inflatable, noncompliant sizing balloon that is oversized with respect to the inside wall of the lumen. The sizing balloon may be cylindrical with a diameter that is oversized with respect to the inside wall of the lumen. The sizing balloon may further be coupled to a pressure sensor for determining the internal pressure in the balloon from the introduction of the expansion medium. In addition, the system may further comprise a measuring means, such as a mass flow meter, for determining the amount of fluid in the sizing balloon.

In some embodiments, each of the individual treatment devices further include an expansion member comprising an inflatable balloon. Generally, each balloon is cylindrical and ranges in diameter from 12 mm to 50 mm when expanded. A balloon within the range is selected based on the measurement made from the sizing balloon so that when the balloon is expanded to its fully inflated shape, it properly engages the wall of the lumen. Typically, the expansion member is inflated with the same medium as the sizing balloon. Optionally, the treatment device may further include a pressure sensor as an extra precaution against over-distension of the organ.

BRIEF DESCRIPTION OF THE DRAWINGS

FIG. 7 is a chart of test results performed on calculating the diameter of a vessel by measuring the volume of air used to inflate the balloon.

DETAILED DESCRIPTION OF THE INVENTION

In various embodiments, the present invention provides methods and systems for measuring, and treating at a controlled and uniform depth, the inner lining of a lumen within a patient. It will be appreciated that the present invention is applicable to a variety of different tissue sites and organs, including but not limited to the esophagus. A treatment apparatus including a sizing member and a treatment device comprising an expandable electrode array is provided. The sizing member is first positioned at a treatment site within the lumen. Once in place, the sizing member is expanded to engage the wall of the lumen to obtain the dimensions of the lumen. The sizing member is removed, and at least a portion of the treatment device is positioned at the tissue site, where the electrode array is expanded to contact the tissue surface according to the measurements made by the sizing member. Sufficient energy is then delivered from the electrode array to impart a desired therapeutic effect, such as cell necrosis, to a discreet layer of tissue.

Various aspects of the invention are similar to the devices and methods disclosed in U.S. application Ser. No. 12/787,324 filed May 25, 2010 and U.S. application Ser. No. 12/259,136 filed Oct. 27, 2008, incorporated herein for all purposes by reference.

Figure 1:
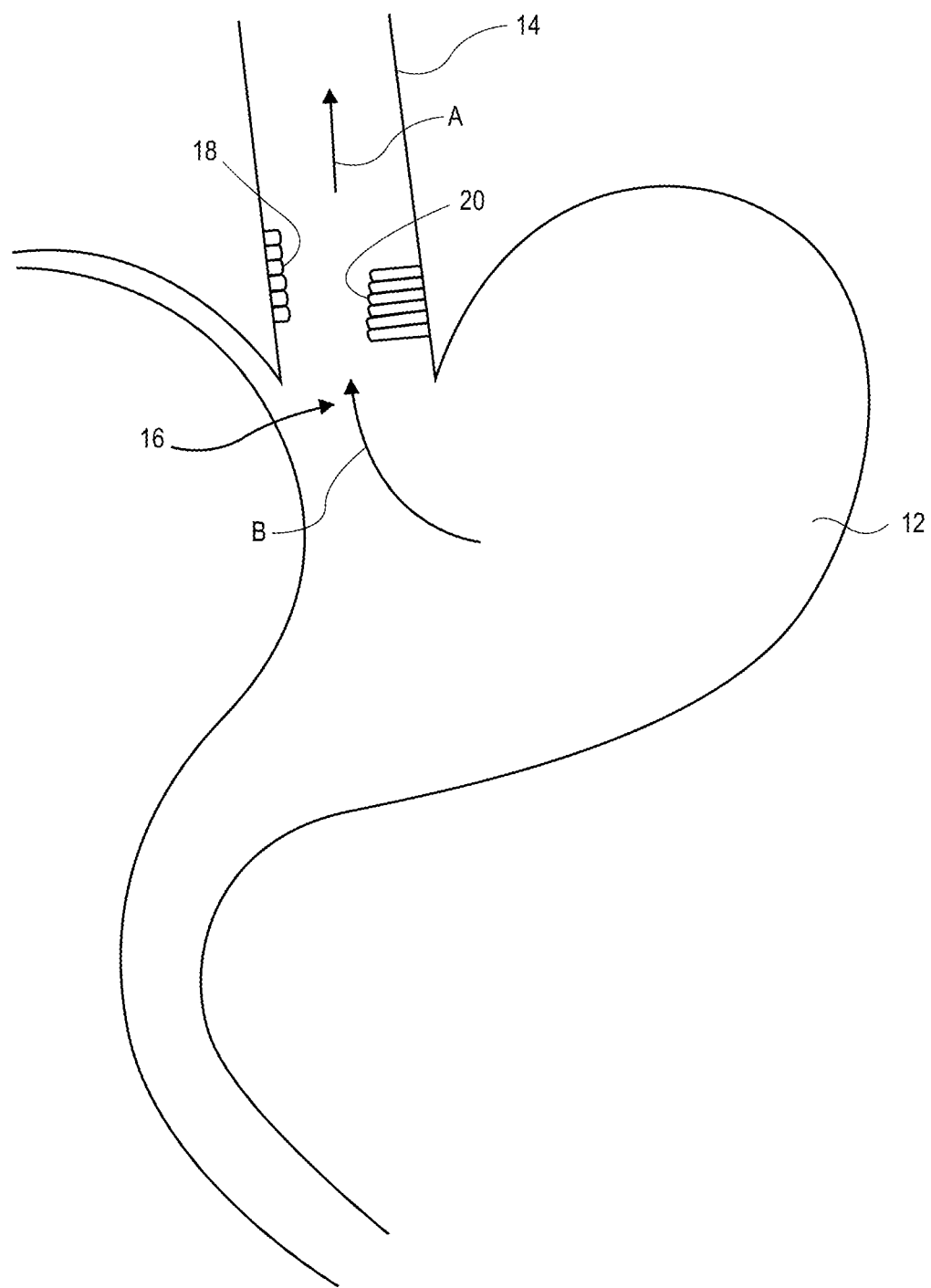
FIG. 1 is a schematic view of portions of an upper digestive tract in a human.

Certain disorders can cause the retrograde flow of gastric or intestinal contents from the stomach 12, into the esophagus 14, as shown by arrows A and B in FIG. 1. Although the causation of these problems are varied, this retrograde flow may result in secondary disorders, such as Barrett's Esophagus, which require treatment independent of and quite different from treatments appropriate for the primary disorder—such as disorders of the lower esophageal sphincter 16. Barrett's esophagus is an inflammatory disorder in which the stomach acids, bile acids and enzymes regurgitated from the stomach and duodenum enter into the lower esophagus causing damage to the esophageal mucosa. When this type of retrograde flow occurs frequently enough, damage may occur to esophageal epithelial cells 18. In some cases the damage may lead to the alteration of the squamous cells, causing them to change into taller specialized columnar epithelial cells 20. This metaplastic change of the mucosal epithelium from squamous cells to columnar cells is called Barrett's esophagus. Although some of the columnar cells may be benign, others may result in adenocarcinoma.

In one aspect, the present invention provides methods and systems for sizing the esophagus and treating columnar epithelium of selected sites of the esophagus in order to mitigate more severe implications for the patient. In many therapeutic procedures according to the present invention, the desired treatment effect is ablation of the tissue. The term "ablation" as used herein means thermal damage to the tissue causing tissue or cell necrosis. However, some therapeutic procedures may have a desired treatment effect that falls short of ablation, e.g. some level of agitation or damage that is imparted to the tissue to inure a desired change in the cellular makeup of the tissue, rather than necrosis of the tissue. With the present invention, a variety of different energy delivery devices can be utilized to create a treatment effect in a superficial layer of tissue, while preserving intact the function of deeper layers, as described hereafter.

Cell or tissue necrosis can be achieved with the use of energy, such as radiofrequency energy, at appropriate levels to accomplish ablation of mucosal or submucosal level tissue, while substantially preserving muscularis tissue. Such ablation is designed to remove the columnar growths 20 from the portions of the esophagus 14 so affected.

Figure 2:
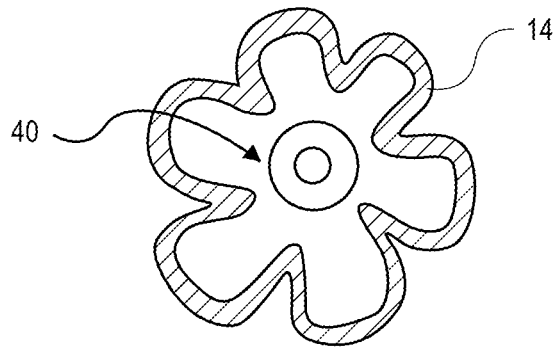
FIG. 2 is a cross sectional view of a device of the invention inserted in to an esophagus in its relaxed, collapsed state.

As illustrated in a cross-sectional view in FIG. 2, the esophagus in its collapsed, relaxed state does not form a perfect, cylindrical tube. Rather, the walls of the esophagus 14 undulate into a plurality of folds. In this state, the diameter of the esophagus is difficult to determine, especially by use of visualization techniques such as ultrasound or optical imaging. Additionally, uniform treatment of target tissue areas is also difficult because of the irregular surface contours of the esophageal wall.

Figure 3:
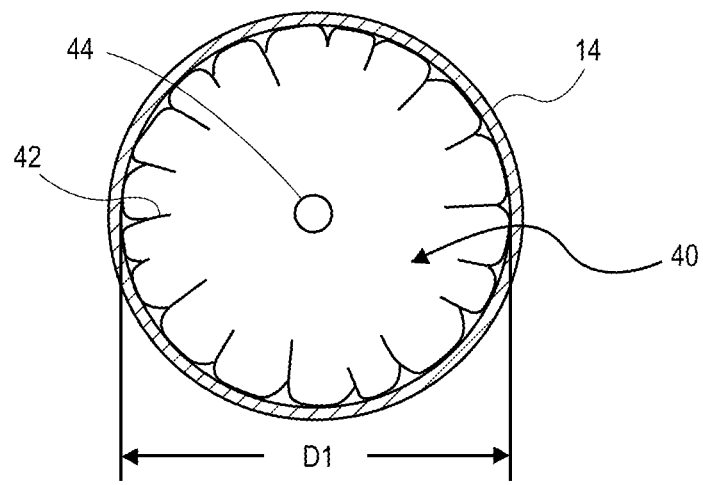
FIG. 3 is a cross-sectional view of a device of the invention deployed in an expanded configuration in the esophagus.
Figure 4:
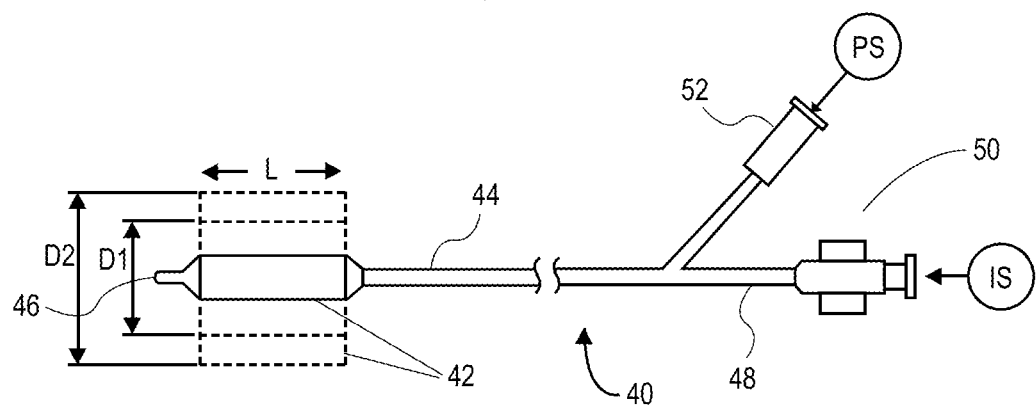
FIG. 4 is a schematic view of a sizing device of the invention.
Figure 5:
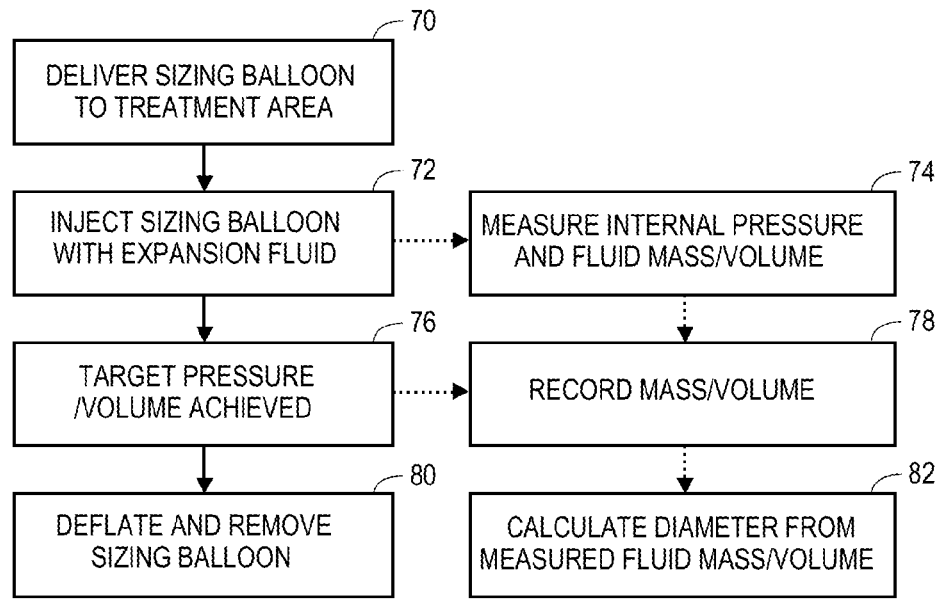
FIG. 5 is a flow chart of a method of the invention for sizing a luminal dimension.

In one embodiment of the invention, as illustrated in FIGS. 2, 3 and 4 and the flow chart of FIG. 5, a method is disclosed for utilizing a sizing device to measure luminal dimensions. The sizing device 40 is first delivered to the treatment region in the body lumen, as shown at block 70. For esophageal sizing as shown in FIG. 2, the esophagus 14 will be in a relaxed or collapsed configuration during delivery of the sizing device. The sizing device 40 is in a collapsed configuration during the delivery of the device to the treatment site in the esophagus. The low profile of the collapsed sizing device 40, as shown in FIG. 2, eases the delivery of the device into the esophagus and minimizes discomfort to the patient. Once the sizing device is oriented in the proper treatment area, an expansion fluid is injected into the balloon, as shown at block 72. The balloon is inflated until it engages the inside wall of the lumen, as shown in FIG. 3. During the infusion of the expansion medium, the extent of engagement of the balloon is monitored, as well as the amount of expansion medium being injected into the balloon, as shown by block 74. Once the balloon properly engages the lumen wall (shown at block 76), the final mass or volume of expansion medium is recorded so that the internal dimension of the esophagus may be calculated, shown at blocks 78, 82. The sizing balloon is then deflated so that it can be readily removed from the treatment site, shown at block 80.

Referring to FIGS. 2, 3, 4, a device of the present invention comprises a sizing device 40 for determining the dimensions of a treatment lumen. The device 40 has an expansion member 42 that is inserted into a lumen in a collapsed configuration and expanded upon proper placement at a pre-selected treatment area. In a preferred configuration, the expansion member 42 is a cylindrical balloon with a native diameter that is oversized so that it will be larger in its fully expanded configuration than the expected diameter of the treatment lumen. The balloon 42 comprises a thin, flexible, bladder made of a material such as polymer, for example polyimide, polyurethane, PET, or the like. The balloon is attached to a catheter sleeve 44, wherein the balloon is disposed on the distal end 46 of the catheter sleeve for infusing an expansion medium into the balloon from an infusion source IS. Infusion source IS is connected to an access port 50 of a y-connector located at the proximal end 48 of the catheter sleeve 44.

Ideally, the expansion medium comprises a compressible fluid, such as air. The expansion medium may alternatively comprise an incompressible fluid, such as water, saline solution, or the like. Infusion of the expansion medium into the sizing balloon may be accomplished by a positive displacement device such as a fluid-infusion pump or calibrated syringe driven by stepper motor or by hand. Alternatively, for a compressible expansion medium, pressurized air or gas may also be used. In many embodiments, the sizing device also comprises a means for determining the amount of expansion fluid transferred to the balloon, such as a calibrated syringe. A mass or volume flow meter may be coupled to the fluid delivery source for simultaneously measuring the amount of fluid in the balloon as it is inflated.

As the expansion medium is injected into balloon 42, the balloon expands radially from its axis to engage the wall of the lumen. For esophageal treatment, the walls of the esophagus 14 unfold to form a more cylindrical shape as balloon 42 expands, as illustrated in FIG. 3. In this configuration, internal diameter D1 of the esophagus 14 is readily calculated based on the length L of the balloon and the measured amount of expansion medium inside the balloon. Balloon 42 is oversized so that the diameter D2 of the balloon when unrestrained and fully inflated is larger than the diameter of the balloon when constrained in the lumen. Although an inflatable balloon is generally preferred, the sizing member may comprise a basket, plurality of struts, calipers, or the like instrument for determining the internal diameter of a tubular member.

Tests were performed to calculate the inside diameter of a member by using volume flow measurements. Various types and sizes of tubes were tested by measuring the mass of air used to inflate an oversized bladder inside the tube. As shown in FIG. 7, the diameter of the tube can be repeatably estimated by measuring the volume of air delivered into the balloon.

In some embodiments of the invention, a pressure sensor may be coupled to the sizing device, wherein the extent of engagement is determined by the internal pressure exerted from the expansion medium as measured by the pressure sensor or visual verification. The pressure sensor may comprise any device for determining the pressure inside a vessel, such as a strain gauge. In FIG. 4, the pressure sensor PS is located at access port 52 at the proximal end of the catheter sleeve 44. Alternatively, the pressure sensor can be located inside the balloon 42. As the balloon expands to engage the wall of the lumen, the pressure in the balloon increases as a result of the constraint on the balloon from the lumen wall. Because the balloon is oversized and not at its fully extended diameter when contacting the lumen wall, the pressure in the balloon is equal to the contact force per unit area against the lumen wall. Therefore, the pressure inside the balloon is directly proportional to the contact force on the lumen wall. Furthermore, the balloon may be expanded to apply pressure to the inside wall of the lumen, thereby causing the lumen to stretch. Generally, the sizing balloon will be inflated to a pressure corresponding to the desired pressure for treatment of the lumen. For esophageal treatment, it is desirable to expand the treatment device sufficiently to occlude the vasculature of the submucosa, including the arterial, capillary, or venular vessels. The pressure to be exerted to do so should therefore be greater than the pressure exerted by such vessels, typically from 1 psig to 10 psig, and preferably from 4 psig to 7 psig.

In some embodiments, the measurement of the pressure inside the balloon may be used to monitor the extent of engagement of the balloon with the lumen wall. Alternatively, the extent of engagement may be monitored by determining the expansion of the balloon via visual inspection with use of an endoscope, or by ultrasound, optical, or fluoroscopic imaging (not shown).

Figure 8:
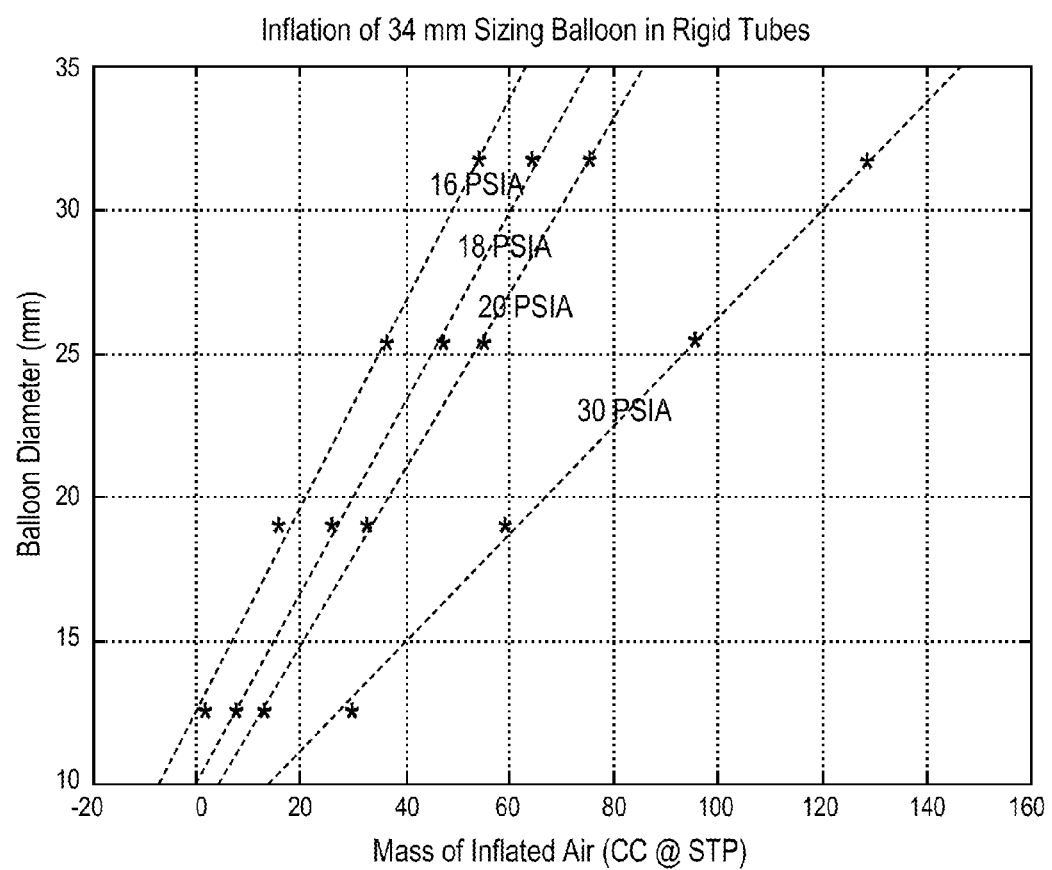
FIG. 8 is a chart of test results for the air mass required to achieve various pressure levels in differently sized rigid containers.

Tests were performed on different sized rigid tubes to calculate the amount of mass required to inflate an oversized balloon in a constrained tube at various pressures. As shown in FIG. 8, the test results showed a predictable linear relationships between the measured inflated air mass and the tube diameter for each pressure range tested.

Figure 6:
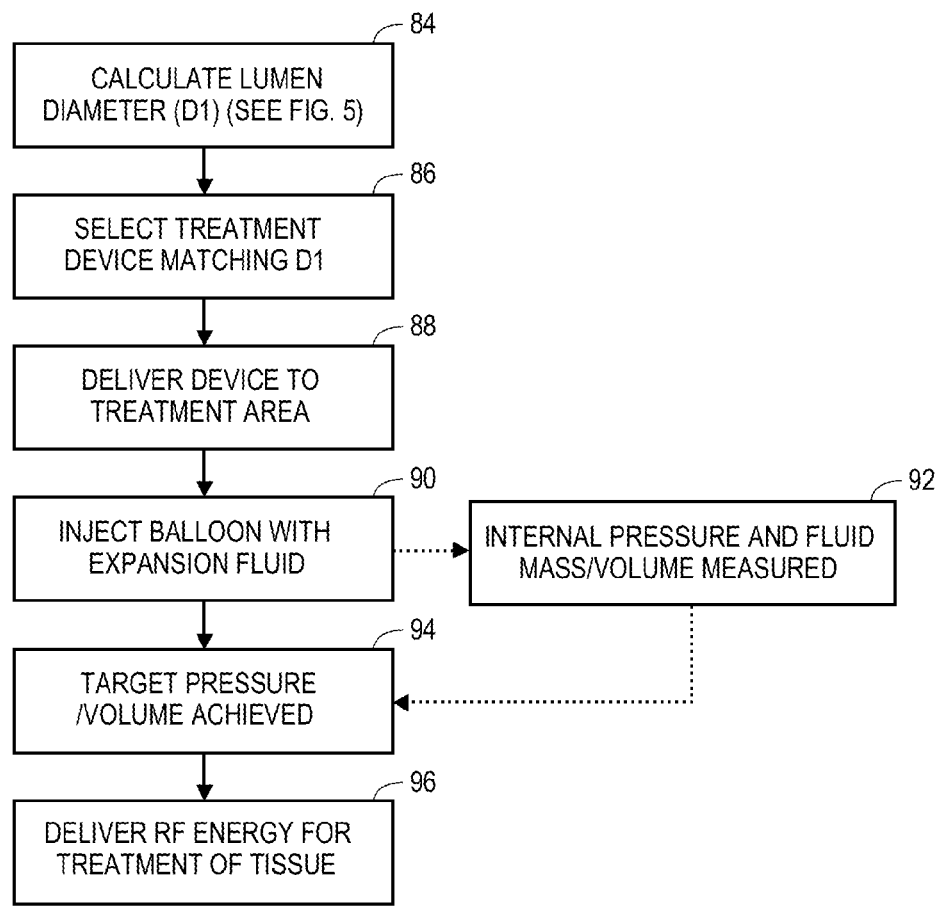
FIG. 6 is a flow chart of a method of the invention for treating luminal tissue.

As shown in the flow chart of FIG. 6, a method and system of the present invention is disclosed for treating a luminal tissue. Similar to the method described in FIG. 5, a sizing device is used to calculate the internal diameter of the lumen, as shown at block 84. The measurement obtained from the sizing device is then used to select a treatment device from an array of different sized catheters, shown at block 86. The device is then inserted into the body lumen and delivered to the treatment site, as shown at block 88. An expansion fluid is then injected into the device by an infusion source like that of the sizing device as shown in block 90. Because the catheter is selected to have an outer diameter when fully expanded that appropriately distends the luminal wall, it is not necessary to monitor the expansion of the catheter. However, the pressure and fluid volume of expansion medium delivered to the treatment device can be monitored as a precautionary measure, as shown in blocks 92 and 94. With the catheter properly engaged to the luminal wall at the treatment site, energy, such as RF energy, is delivered to the catheter for treatment of the luminal tissue, as shown at block 96. Once treatment has been administered, the catheter is deflated for removal from the lumen as shown in block 98.

Figure 9:
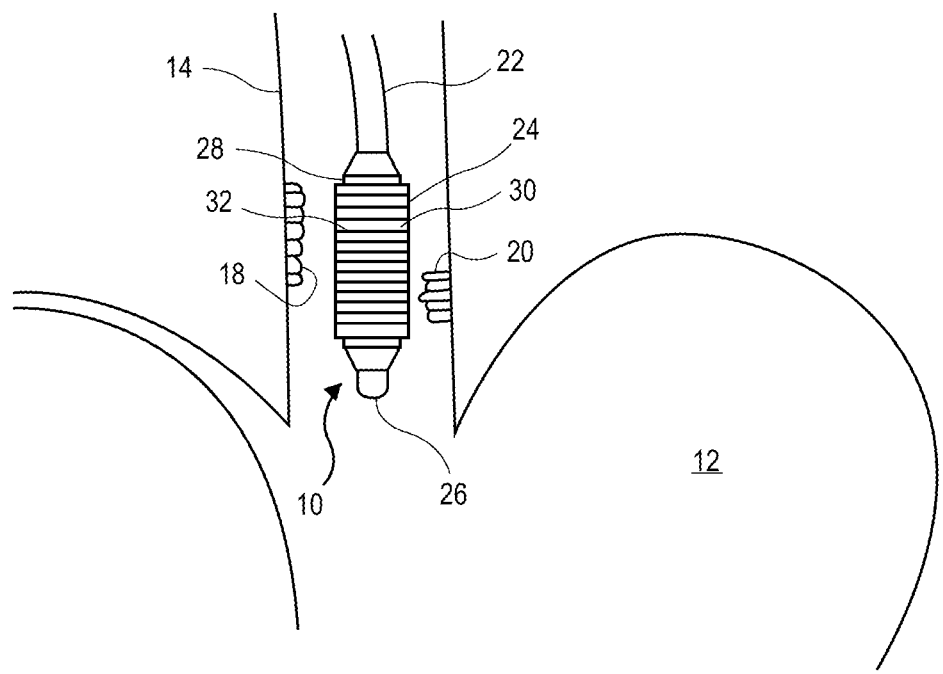
FIG. 9 is a schematic view of a treatment device of the invention in a compressed configuration in the esophagus.
Figure 10:
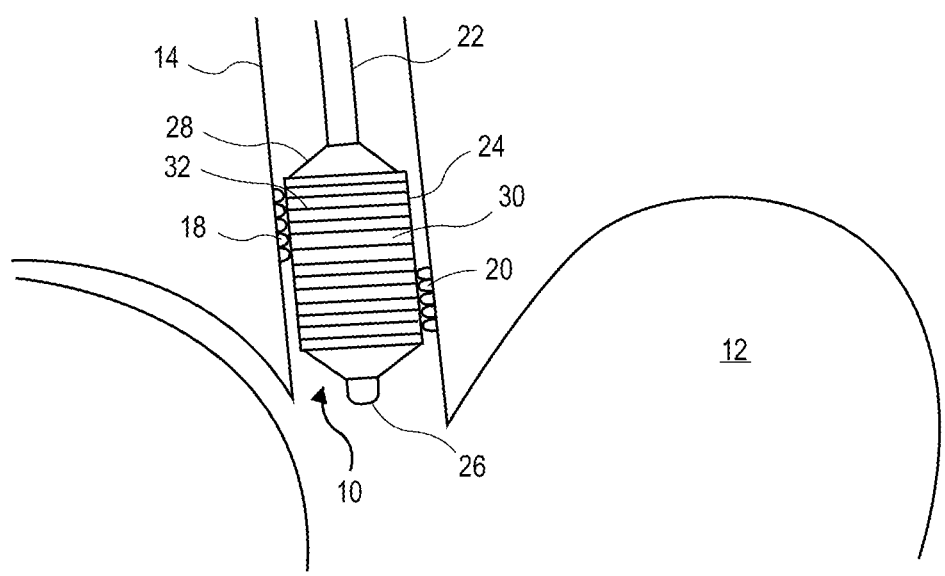
FIG. 10 is a schematic view of a treatment device of the invention in an expanded configuration in the esophagus.

As illustrated in FIGS. 9 and 10, a treatment device 10 constructed in accordance with the principles of the present invention, includes an elongated catheter sleeve 22, that is configured to be inserted into the body in any of various ways selected by the medical provider. For treatment of the esophagus, the treatment device may be placed, (i) endoscopically, e.g. through esophagus 14, (ii) surgically or (iii) by other means.

When an endoscope (not shown) is used, catheter sleeve 22 can be inserted in the lumen of the endoscope, or catheter sleeve 22 can be positioned on the outside of the endoscope. Alternately, an endoscope may be used to visualize the pathway that catheter 22 should follow during placement. As well, catheter sleeve 22 can be inserted into esophagus 14 after removal of the endoscope.

An electrode support 24 is provided and can be positioned at a distal end 26 of catheter sleeve 22 to provide appropriate energy for ablation as desired. Electrode support 24 has a plurality of electrode area segments 32 attached to the surface of the support. The electrodes 32 can be configured in an array 30 of various patterns to facilitate a specific treatment by controlling the electrode size and spacing (electrode density). In various embodiments, electrode support 24 is coupled to an energy source configured for powering the array 30 at levels appropriate to provide the selectable ablation of tissue to a predetermined depth of tissue. The energy may be delivered circumferentially about the axis of the treatment device in a single step, i.e., all at one time. Alternatively, the energy may be delivered to different circumferential and/or axial sections of the esophageal wall sequentially.

In many embodiments, the support 24 may comprise a flexible, non-distensible backing. For example, the support 24 may comprise of a thin, rectangular sheet of polymer materials such as polyimide, polyester or other flexible thermoplastic or thermosetting polymer film. The support 24 may also comprise polymer covered materials, or other nonconductive materials. Additionally, the backing may include an electrically insulating polymer, with an electro-conductive material, such as copper, deposited onto a surface so that an electrode pattern can be etched into the material to create an array of electrodes.

Electrode support 24 can be operated at a controlled distance from, or in direct contact with the wall of the tissue site. This can be achieved by coupling electrode support 24 to an expandable member 28, which has a cylindrical configuration with a known, fixed length, and a diameter sized to match at its expanded state the calculated diameter of the expanded (not collapsed) lumen. Suitable expandable members include but are not limited to a balloon, non-compliant balloon, balloon with a tapered geometry, cage, frame, basket, plurality of struts, expandable member with a furled and an unfurled state, one or more springs, foam, bladder, backing material that expands to an expanded configuration when unrestrained, and the like. For esophageal treatment, it is desirable to expand the expandable member to distend the lumen sufficiently to occlude the vasculature of the submucosa, including the arterial, capillary, or venular vessels. The pressure to be exerted to do so should therefore be greater than the pressure exerted by such vessels, typically from 1 psig to 10 psig, and preferably from 4 psig to 7 psig. Generally, the expandable member for the treatment device will be selected to match the diameter measured by the sizing device at the desired pressure. Under this configuration, full expansion of the expandable member will result in the a pressure that properly distends the luminal wall. In some embodiments, it may be desirable to employ a pressure sensor or mass flow meter (not shown) as a precautionary measure so that overdistension of the lumen does not occur.

As shown in FIGS. 9 and 10, the electrode support 24 is wrapped around the circumference of expandable member 28. In one system of the present invention, a plurality of expandable members can be provided wherein the diameter of the expandable member varies from 12 mm to 50 mm when expanded. Accordingly, the system may include a plurality of electrode supports, each sized differently corresponding to the different sized expandable members. Alternatively, the electrode support 24 may be oversized to be at least large enough to cover the circumference of the largest expandable member. In such a configuration, the electrode support overlaps itself as it is wrapped around the circumference of the expandable member, similar to the electrode support of device 100 illustrated in FIG. 11, discussed infra.

In another embodiment, expandable member 28 is utilized to deliver the ablation energy itself. An important feature of this embodiment includes the means by which the energy is transferred from distal end 26 to expandable member 28. By way of illustration, one type of energy distribution that can be utilized is disclosed in U.S. Pat. No. 5,713,942, incorporated herein by reference, in which an expandable balloon is connected to a power source, which provides radio frequency power having the desired characteristics to selectively heat the target tissue to a desired temperature. Expandable member 28 may be constructed from electrically insulating polymer, with an electro-conductive material, such as copper, deposited onto a surface so that an electrode pattern can be etched into the material to create an array of electrodes.

Electrode support 24 can deliver a variety of different types of energy including but not limited to, radio frequency, microwave, ultrasonic, resistive heating, chemical, a heatable fluid, optical including without limitation, ultraviolet, visible, infrared, collimated or non collimated, coherent or incoherent, or other light energy, and the like. It will be appreciated that the energy, including but not limited to optical, can be used in combination with one or more sensitizing agents.

The depth of treatment obtained with treatment device 10 can be controlled by the selection of appropriate treatment parameters by the user as described in the examples set forth herein. One important parameter in controlling the depth of treatment is the electrode density of the array 30. As the spacing between electrodes decreases, the depth of treatment of the affected tissue also decreases. Very close spacing of the electrodes assures that the current and resulting ohmic heating in the tissue is limited to a very shallow depth so that injury and heating of the submucosal layer are minimized. For treatment of esophageal tissue using RF energy, it may be desirable to have a width of each RF electrode to be no more than, (i) 3 mm, (ii) 2 mm, (iii) 1 mm (iv) 0.5 mm or (v) 0.3 mm (vi) 0.1 mm and the like. Accordingly, it may be desirable to have a spacing between adjacent RF electrodes to be no more than, (i) 3 mm, (ii) 2 mm, (iii) 1 mm (iv) 0.5 mm or (v) 0.3 mm (vi) 0.1 mm and the like. The plurality of electrodes can be arranged in segments, with at least a portion of the segments being multiplexed. An RF electrode between adjacent segments can be shared by each of adjacent segments when multiplexed.

Figure 13A:
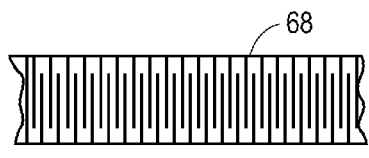
FIG. 13 shows the electrode patterns that may be used with a treatment device of the invention.
Figure 13B:
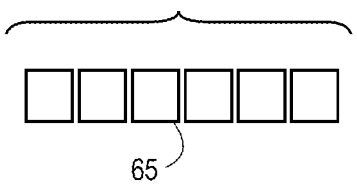
Figure 13C:
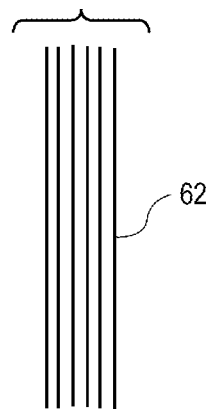
Figure 14A:
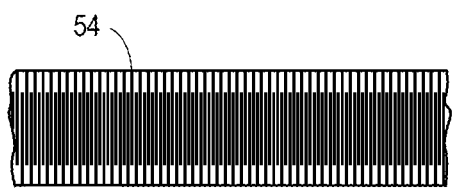
FIG. 14 shows additional electrode patterns that may be used with a treatment device of the invention.
Figure 14B:
Figure 14D:
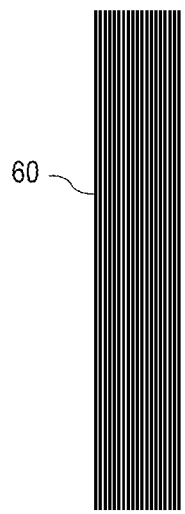
Figure 14C:
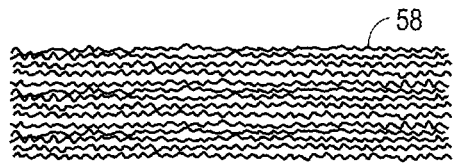

The electrode patterns of the present invention may be varied depending on the length of the site to be treated, the depth of the mucosa and submucosa, in the case of the esophagus, at the site of treatment and other factors. The electrode pattern 30 may be aligned in axial or traverse direction across the electrode support 24, or formed in a linear or non-linear parallel matrix or series of bipolar pairs or monopolar electrodes. One or more different patterns may be coupled to various locations of expandable member 28. For example, an electrode array, as illustrated in FIGS. 13(a) through 13(c), may comprise a pattern of bipolar axial interlaced finger electrodes 68, six bipolar rings 62 with 2 mm separation, or monopolar rectangles 65 with 1 mm separation. Other suitable RF electrode patterns which may be used include, without limitation, those patterns shown in FIGS. 14(a) through 14(d) as 54, 56, 58 and 60, respectively. Pattern 54 is a pattern of bipolar axial interlaced finger electrodes with 0.3 mm separation. Pattern 56 includes monopolar bands with 0.3 mm separation. Pattern 60 includes bipolar rings with 0.3 mm separation. Pattern 58 is electrodes in a pattern of undulating electrodes with 0.2548 mm separation.

A probe sensor may also be used with the system of the present invention to monitor and determine the depth of ablation. In one embodiment, one or more sensors (not shown), including but not limited to thermal and the like, can be included and associated with each electrode segment 32 in order to monitor the temperature from each segment and then be used for control. The control can be by way of an open or closed loop feedback system. In another embodiment, the electroconductive member can be configured to permit transmission of microwave energy to the tissue site. Treatment apparatus 10 can also include steerable and directional control devices, a probe sensor for accurately sensing depth of ablation, and the like.

Figure 11:
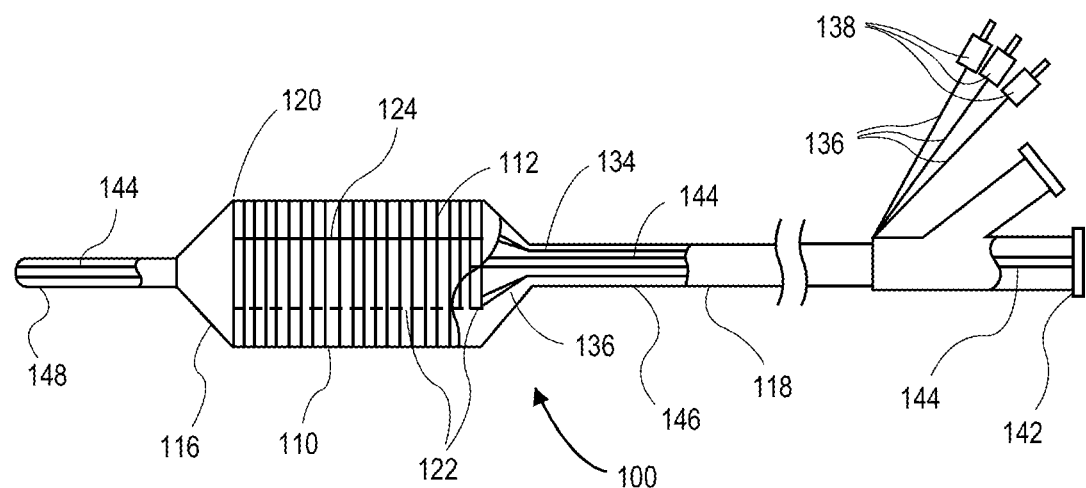
FIG. 11 is a schematic view of another embodiment of a treatment device of the invention.

Referring to FIG. 11, one embodiment of the invention comprises an electrode deployment device 100 having an electrode support 110 furled around the outside of an inflatable balloon 116 that is mounted on a catheter sleeve 118. Support 110 has an electrode array 112 etched on its surface, and is aligned between edges 120 that intersect the taper region located at the distal and proximal ends of balloon 116. Support 110 may be attached at a first end 122 to balloon 116 with an adhesive. The second end 124 of the support is furled around the balloon, overlapping the first end 122. Alternatively, support 110 may be retained in a compressed furled state around balloon 116 by an elastic band. In such a configuration, the adhesive need not be applied to attach first end 122 to balloon 116, thus allowing for rapid placement or exchange of the appropriately sized balloon 116 to match measurements made from the sizing device 10 illustrated in FIG. 4.

Figure 12:
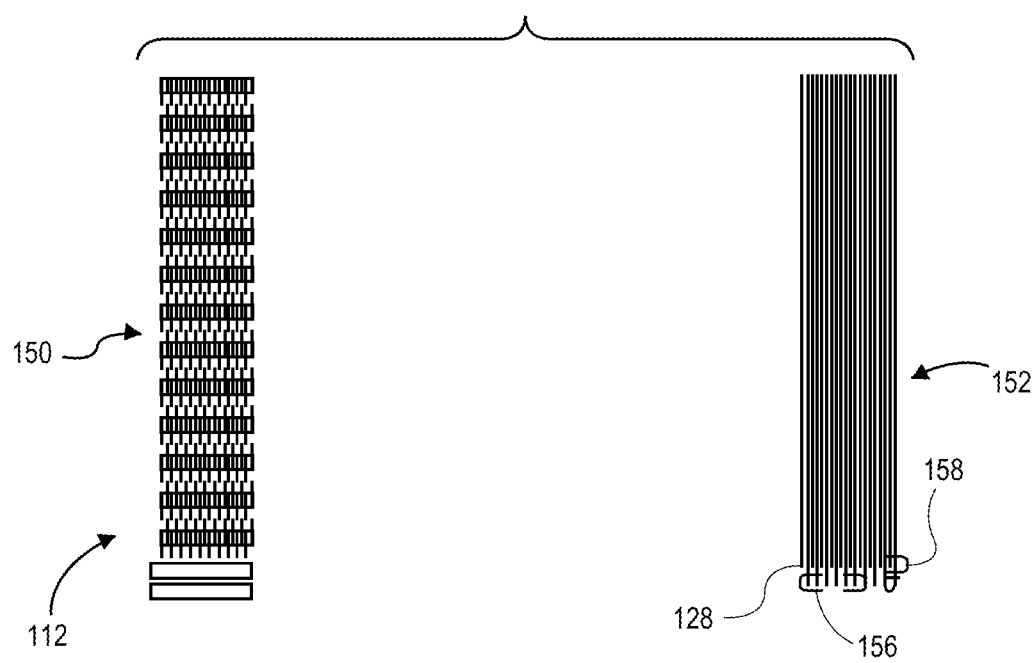
FIG. 12 shows a top view and a bottom view of an electrode pattern of the device of FIG. 11.

FIG. 12 shows a bottom view 150 and a top view 152 of the electrode array 112 of support 110. In this embodiment, the array 112 has 20 parallel bars, 0.25 mm wide, separated by gaps of 0.3 mm. The bars on the circuit form twenty complete continuous rings around the circumference of balloon 116. Electrode array 112 can be etched from a laminate consisting of copper on both sides of a polyimide substrate. One end of each copper bar has a small plated through hole 128, which allows signals to be passed to these bars from 1 of 2 copper junction blocks 156 and 158, respectively, on the back of the laminate. One junction block 156 is connected to all of the even numbered bars, while the other junction block 158 is connected to all of the odd numbered bars.

As shown in FIGS. 11 and 12, each junction block 156 and 158 is then wired to a bundle of AWG wires 134. The wiring is external to balloon 116, with the distal circuit wires affixed beneath the proximal circuit. Upon meeting the catheter sleeve of the device, these bundles 134 can be soldered to three litz wire bundles 136. One bundle 136 serves as a common conductor for both circuits while the other two bundles 136 are wired individually to each of the two circuits. The litz wires are encompassed with heat shrink tubing along the entire length of the catheter sleeve 118 of the device. Upon emerging from the proximal end of the catheter sleeve, each of these bundles 136 is individually insulated with heat shrink tubing before terminating to a mini connector plug 138. Under this configuration, power can be delivered to either or both of the two bundles so that treatment can be administered to a specific area along the array.

The y connector 142 at the proximal end of the catheter sleeve includes access ports for both the thru lumen 144 and the inflation lumen 146. The thru lumen spans the entire length of the balloon catheter and exits through lumen tip 148 at the distal end of balloon 116. The inflation lumen 146 is coupled to balloon 116 so that the balloon can be inflated by delivery of a liquid, gaseous solution such as air, or the like.

In some embodiments, for delivery of apparatus 100, support 110 is tightly furled about deflated balloon 116 and placed with within a sheath (not shown). During deployment, this sheath is retracted along the shaft to expose support 110. In alternative embodiments, an elastic member (not shown) may be coupled to the support 110 to keep the support furled around balloon 116 during deployment of apparatus 100.

In order to ensure good contact between the esophageal wall and electrode array 112, slight suction may be applied to the through lumen tube to reduce the air pressure in the esophagus 14 distal to balloon 116. The application of this slight suction can be simultaneously applied to the portion of the esophagus 14 proximal to balloon 116. This suction causes the portion of the esophageal wall distended by balloon 116 to be pulled against electrode arrays 112 located on balloon 116.

Apparatus 100, illustrated in FIG. 11, is designed for use with the RF energy methods as set forth herein. Electrode array 112 can be activated with approximately 300 watts of radio frequency power for the length of time necessary to deliver an energy density per cm$^2$ from J/cm$^2$ to 50 J/cm$^2$. To determine the appropriate level of energy, the diameter of the lumen is evaluated so that the total treatment area can be calculated. A typical treatment area will require total energy density per cm$^2$ ranging from 1 J/cm$^2$ to 50 J/cm$^2$.

In order to effectively ablate the mucosal lining of the esophagus and allow re-growth of a normal mucosal lining without creating damage to underlying tissue structures, it is preferable to deliver the radiofrequency energy over a short time span in order to reduce the effects of thermal conduction of energy to deeper tissue layers, thereby creating a "searing" effect. It is preferable to deliver the radiofrequency energy within a time span of less than 5 seconds. An optimal time for effective treatment is less than 1 second, and preferably less than 0.5 second or 0.25 seconds. The lower bound on time may be limited by the ability of the RF power source to deliver high powers. Since the electrode area and consequently the tissue treatment area can be as much as several square centimeters, RF powers of several hundred watts would be required in order to deliver the desired energy density in short periods of time. This may pose a practical limitation on the lower limit of time. However, an RF power source configured to deliver a very short, high power, pulse of energy could be utilized. Using techniques similar to those used for flash lamp sources, or other types of capacitor discharge sources, a very high power, short pulse of RF energy can be created. This would allow treatment times of a few msec. or less. While this type of approach is feasible, in practice a more conventional RF source with a power capability of several hundred watts may be preferred.

The energy source may be manually controlled by the user and is adapted to allow the user to select the appropriate treatment time and power setting to obtain a controlled depth of ablation. The energy source can be coupled to a controller (not shown), which may be a digital or analog controller for use with the energy source, including but not limited to an RF source, or a computer with software. When the computer controller is used it can include a CPU coupled through a system bus. The system may include a keyboard, a disk drive, or other non volatile memory system, a display and other peripherals known in the art. A program memory and a data memory will also be coupled to the bus.

In some embodiments of the present invention, systems and methods are disclosed for treating luminal tissue with a single treatment device that variably expands to accommodate a number of different sized lumens. Preferably, the treatment device comprises a furled electrode support that variably engages the luminal wall while keeping the electrode density constant. Such approaches are described in detail in application Ser. No. 10/754,444, published as U.S. publication no. 2005/0171524, the full disclosure of which is incorporated herein by reference. For example, for the treatment device 100 shown in FIG. 11, which employs a variable exposed-length electrode array 112, balloon 116 may be oversized with respect to the size of the lumen so that it can be expanded to accommodate differing luminal dimensions from patient to patient. Measurements from sizing device 10 can be used to scale as needed the desired power and energy settings to deliver the same power and energy per unit area. These changes can be made either automatically or from user input to the RF power source. If different treatment depths are desired, the geometry of electrode array 112 can be modified to create either a deeper or more superficial treatment region.

Making the electrodes of array 112 more narrow and spacing the electrodes closer together reduces the treatment depth. Making the electrodes of array 112 wider, and spacing the electrodes further apart, increases the depth of the treatment region. Non-uniform widths and spacings may be exploited to achieve various treatment effects.

Figure 15:
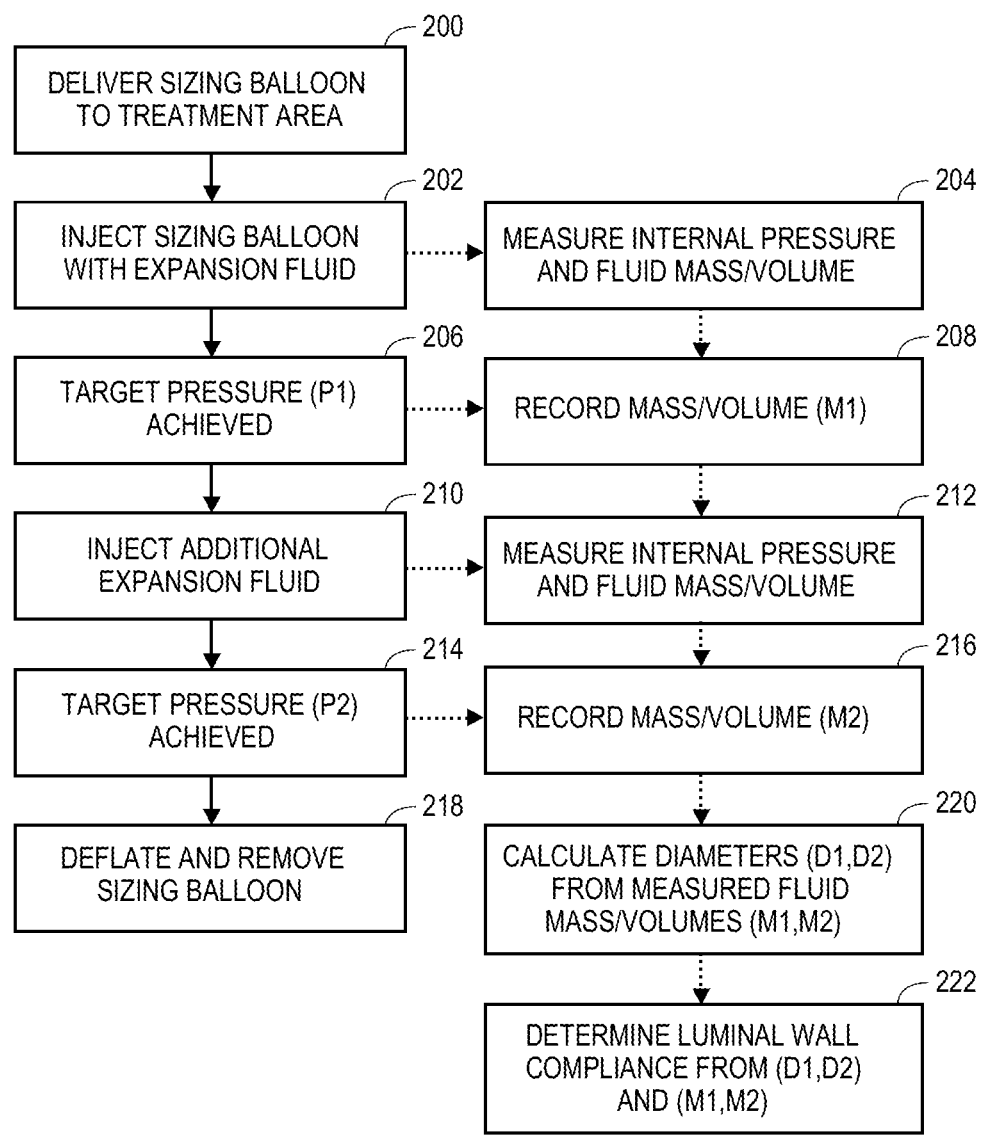
FIG. 15 shows a flow chart of a method of the invention for determining the wall compliance of a lumen.

Referring to FIG. 15, the sizing device may be used as a method for determining the lumen diameter and wall compliance of one or more sections of the esophagus. A sizing device having an inflatable balloon like that of device 40 illustrated in FIG. 5 is inserted into the esophagus in a compressed configuration and positioned at a location within the esophagus, as shown at block 200. The balloon is then inflated with a compressible fluid so that the balloon engages the inside wall of the esophagus and distends the wall of the esophagus, shown at block 202. While the expansion medium is delivered to the balloon, the static pressure inside the balloon is monitored with a pressure sensor and the amount of expansion medium delivered to the balloon is measured, shown at block 204. The pressure may be measured at the infusion source with strain gauge or the like. Alternatively, the pressure can be measured at a location inside the balloon with a microminiature pressure transducer or the like. The amount of expansion medium delivered to the balloon may comprise a mass-flow meter or the like. Once a first target pressure (P1) inside the balloon is achieved, a corresponding first mass or volume measurement (M1) is recorded, as shown at blocks 206 and 208. The values of P1 and Ml are used to calculate the lumen diameter at pressure P1, using the relationship previously determined and shown in FIG. 8, block 200 of FIG. 15, or other equivalent means. Additional expansion medium is then delivered to the balloon, and the static pressure and the total amount of expansion medium within the balloon are monitored, shown at blocks 210 and 212. This continues until a second target pressure (P2) inside the balloon is achieved, and a corresponding second mass or volume measurement (M2) is recorded, as shown at blocks 214 and 216. Calculation of the lumen diameter at pressure P2 is performed as previously described and shown in block 220. The sizing balloon is then deflated and then removed from the esophagus as shown in block 218. Target pressure values P1 and P2 are generally set at values that cause the esophagus to distend, but not overdistend. Typical target pressure values range from 1 psig to 7 psig, preferably 4 psig to 7 psig. Wall compliance of the esophagus is then determined based on the variation in the calculated lumen diameter between a first measured pressure P1 and a second measured pressure P2, as shown in block 222.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A system for treating abnormal tissue at a treatment location, comprising:
    an electrode support comprising a flexible, non-distensible backing with a pre-deployed state and a deployed state, a size of the electrode support in the deployed state selected to engage a wall of an esophageal body lumen;
    an inflatable member around which the electrode support is wrapped such that the electrode support extends continuously around a circumference of the inflatable member and continuously covers the circumference along a length of the inflatable member between a distal end and a proximal end of the inflatable member; and an electrode pattern positioned on the electrode support such that the electrode pattern wraps around a circumference of the electrode support and adapted to deliver energy to at least a portion of the engaged wall of the esophageal body lumen at a treatment location.

2. The system of claim 1, wherein a size of the electrode support in the pre-deployed state is selected for insertion and movement of the electrode support in the body lumen.

3. The system of claim 1, wherein a size of the electrode support in the pre-deployed state is selected for insertion in a lumen of an endoscope.

4. The system of claim 1, wherein the abnormal tissue is Barrett's esophagus.

5. The system of claim 1, wherein the electrode pattern comprises a plurality of bipolar pairs.

6. The system of claim 1, wherein the electrode pattern comprises a plurality of bipolar rings.

7. The system of claim 1, wherein the electrode pattern comprises a plurality of bipolar axial interlaced fingers electrodes.

8. The system of claim 1, wherein the electrode pattern comprises a plurality of electrodes with a spacing between adjacent electrodes no more than 3 mm.

9. The system of claim 8, wherein the plurality of electrodes includes a spacing between adjacent electrodes no more than 2 mm.

10. The system of claim 1, wherein the inflatable member comprises a cylindrical inflatable member.

11. A device for treating abnormal tissue at a treatment location, comprising:
an electrode support comprising a flexible, non-distensible backing with a pre-deployed state and a deployed state, a size of the electrode support in the deployed state selected to engage a wall of an esophageal body lumen; and
an inflatable member around which the electrode support is wrapped such that the electrode support extends continuously around a circumference of the inflatable member and continuously covers the circumference along a length of the inflatable member between a distal end and a proximal end of the inflatable member; and
an electrode pattern positioned on the electrode support and adapted to deliver energy to at least a portion of the engaged wall of the esophageal body lumen at a treatment location, wherein the electrode pattern includes at least a plurality of bipolar rings or bipolar axial interlaced finger electrodes.

12. The device of claim 11, wherein a size of the electrode support in the pre-deployed state is selected for insertion and movement of the electrode support in the body lumen.

13. The device of claim 11, wherein a size of the electrode support in the pre-deployed state is selected for insertion in a lumen of an endoscope.

14. The device of claim 11, wherein the abnormal tissue is Barrett's esophagus.

15. The device of claim 11, wherein the electrode pattern wraps around a circumference of the electrode support.

16. The device of claim 11, wherein the electrode pattern comprises a plurality of electrodes with a spacing between adjacent electrodes no more than 3 mm.

17. The device of claim 16, wherein the plurality of electrodes include a spacing between adjacent electrodes no more than 2 mm.

18. The device of claim 11, wherein the inflatable member comprises a cylindrical inflatable member.

* * * * *